US007061615B1

(12) United States Patent
Lowe-Webb

(10) Patent No.: US 7,061,615 B1
(45) Date of Patent: Jun. 13, 2006

(54) SPECTROSCOPICALLY MEASURED OVERLAY TARGET

(75) Inventor: Roger R. Lowe-Webb, Sunnyvale, CA (US)

(73) Assignee: Nanometrics Incorporated, Milpitas, CA (US)

( * ) Notice: Subject to any disclaimer, the term of this patent is extended or adjusted under 35 U.S.C. 154(b) by 504 days.

(21) Appl. No.: 09/960,892

(22) Filed: Sep. 20, 2001

(51) Int. Cl.
  *G01B 11/00* (2006.01)
(52) U.S. Cl. .................... 356/401; 430/22; 430/30; 257/797
(58) Field of Classification Search ........ 356/400–401; 430/2, 22, 30
See application file for complete search history.

(56) References Cited

U.S. PATENT DOCUMENTS

| | | | |
|---|---|---|---|
| 4,141,780 A | 2/1979 | Kleinknecht et al. ........ 156/626 |
| 4,172,664 A | 10/1979 | Charsky et al. ............. 356/356 |
| 4,408,884 A | 10/1983 | Kleinknecht et al. ........ 356/355 |
| 4,555,767 A | 11/1985 | Case et al. .................. 364/563 |
| 4,593,368 A | 6/1986 | Fridge et al. ................ 364/525 |
| 4,672,196 A | 6/1987 | Canino ....................... 250/225 |
| 4,707,610 A | 11/1987 | Lindow et al. ............. 250/560 |
| 4,748,335 A | 5/1988 | Lindow et al. ............. 250/572 |
| 5,007,708 A | 4/1991 | Gaylord et al. ........... 350/162.2 |
| 5,035,770 A | 7/1991 | Braun ......................... 156/643 |
| 5,042,949 A | 8/1991 | Greenberg et al. .......... 356/345 |
| 5,042,951 A | 8/1991 | Gold et al. .................. 356/369 |
| 5,045,704 A | 9/1991 | Coates ....................... 250/372 |
| 5,164,790 A | 11/1992 | McNeil et al. ............. 356/355 |
| 5,191,216 A | 3/1993 | Henderson et al. .......... 257/28 |
| 5,214,492 A | 5/1993 | LoBianco et al. .......... 356/400 |
| 5,216,257 A | 6/1993 | Brueck et al. ............. 250/548 |
| 5,216,680 A | 6/1993 | Magnusson et al. .......... 372/20 |
| 5,307,152 A | 4/1994 | Boehnlein et al. .......... 356/376 |
| 5,337,146 A | 8/1994 | Azzam ....................... 356/367 |
| 5,349,440 A | 9/1994 | DeGroot .................... 356/349 |
| RE34,783 E | 11/1994 | Coates ....................... 250/372 |
| 5,363,171 A | 11/1994 | Mack .......................... 355/68 |
| 5,555,474 A | 9/1996 | Ledger ....................... 356/381 |
| 5,559,598 A * | 9/1996 | Matsumoto ................. 356/490 |
| 5,559,601 A | 9/1996 | Gallatin et al. ............. 356/363 |
| 5,596,406 A | 1/1997 | Rosenewaig et al. ....... 356/327 |
| 5,596,413 A * | 1/1997 | Stanton et al. ............. 356/401 |

(Continued)

FOREIGN PATENT DOCUMENTS

EP  0 402 191 A1  12/1990

(Continued)

OTHER PUBLICATIONS

Bischoff, J. et al., "Light Diffraction Based Overlay Measurement" *Proceedings of SPIE* vol. 4344 (2001) pp. 222-233.

(Continued)

*Primary Examiner*—Layla G. Lauchman
(74) *Attorney, Agent, or Firm*—Silicon Valley Patent Group LLP

(57) ABSTRACT

An overlay target for spectroscopic measurement includes at least two diffraction gratings, one grating overlying the other. The diffraction gratings may include an asymmetry relative to each other in order to improve resolution of the presence as well as the direction of any mis-registration. For example, the asymmetry between the two diffraction gratings may be a phase offset, a difference in pitch, line width, etc. The overlay target may be spectroscopically measuring, for example, using an optical model and a best fit analysis. Moreover, the overlay target may be optimized by modeling the overlay target and adjusting the variable parameters and calculating the sensitivity of the overlay target to changes in variable parameters.

13 Claims, 11 Drawing Sheets

U.S. PATENT DOCUMENTS

| | | | |
|---|---|---|---|
| 5,607,800 A | 3/1997 | Ziger | 430/8 |
| 5,646,730 A | 7/1997 | Mitchell et al. | 356/356 |
| 5,739,909 A | 4/1998 | Blayo et al. | 356/369 |
| 5,747,813 A | 5/1998 | Norton et al. | 250/372 |
| 5,805,290 A | 9/1998 | Ausschnitt et al. | 356/401 |
| 5,841,139 A | 11/1998 | Sostek et al. | 250/339.12 |
| 5,867,276 A | 2/1999 | McNeil et al. | 356/445 |
| 5,880,838 A | 3/1999 | Marx et al. | 356/351 |
| 5,889,593 A | 3/1999 | Bareket | 356/445 |
| 5,900,633 A | 5/1999 | Solomon et al. | 250/339.08 |
| 5,963,329 A | 10/1999 | Conrad et al. | 356/372 |
| 5,969,819 A | 10/1999 | Wang | 356/371 |
| 6,031,614 A | 2/2000 | Michaelis et al. | 356/369 |
| 6,077,756 A | 6/2000 | Lin et al. | 438/401 |
| 6,079,256 A * | 6/2000 | Bareket | 73/105 |
| 6,084,712 A | 7/2000 | Harding | 359/618 |
| 6,097,488 A | 8/2000 | Grek et al. | 356/364 |
| 6,100,985 A | 8/2000 | Scheiner et al. | 356/381 |
| 6,130,750 A | 10/2000 | Ausschnitt et al. | 356/401 |
| 6,281,974 B1 | 8/2001 | Scheiner et al. | 356/381 |
| 6,366,861 B1 | 4/2002 | Waldhauer et al. | 702/35 |
| 6,407,396 B1 | 6/2002 | Mih et al. | 250/491.1 |
| 6,429,930 B1 | 8/2002 | Littaue et al. | 356/124 |
| 6,429,943 B1 | 8/2002 | Opsal et al. | 356/625 |
| 6,433,878 B1 | 8/2002 | Niu et al. | 356/603 |
| 6,458,605 B1 | 10/2002 | Stirton | 438/7 |
| 6,476,920 B1 | 11/2002 | Scheiner et al. | 356/630 |
| 6,483,580 B1 | 11/2002 | Xu et al. | 356/300 |
| 6,556,947 B1 | 4/2003 | Scheiner et al. | 702/172 |
| 6,699,624 B1 * | 3/2004 | Niu et al. | 430/5 |
| 2002/0018217 A1 | 2/2002 | Weber-Grabau et al. | 356/601 |
| 2002/0024669 A1 | 2/2002 | Danner et al. | 356/369 |
| 2002/0033945 A1 | 3/2002 | Xu et al. | 356/369 |
| 2002/0033954 A1 | 3/2002 | Niu et al. | 356/601 |
| 2002/0035455 A1 | 3/2002 | Niu et al. | 703/4 |
| 2002/0038196 A1 | 3/2002 | Johnson et al. | 702/179 |
| 2002/0051564 A1 | 5/2002 | Benesh et al. | 382/145 |
| 2002/0105646 A1 | 8/2002 | Zhao et al. | 356/369 |
| 2002/0113966 A1 | 8/2002 | Shchegrov et al. | 356/369 |
| 2002/0135875 A1 | 9/2002 | Niu et al. | 359/564 |
| 2002/0149782 A1 | 10/2002 | Raymond | 356/616 |
| 2002/0158193 A1 | 10/2002 | Sezginer et al. | 250/237 |
| 2003/0002043 A1 | 1/2003 | Abdulhalim et al. | 356/400 |
| 2003/0020912 A1 | 1/2003 | Norton et al. | 356/369 |
| 2003/0042579 A1 | 3/2003 | Schulz | 257/629 |
| 2003/0043372 A1 | 3/2003 | Schulz | 356/327 |
| 2003/0043375 A1 | 3/2003 | Opsal | 356/369 |
| 2003/0044702 A1 | 3/2003 | Schulz | 430/30 |
| 2003/0160163 A1 | 8/2003 | Wong et al. | 250/237 |
| 2003/0169423 A1 | 9/2003 | Finarov et al. | 250/237 |
| 2003/0223630 A1 | 12/2003 | Adel et al. | 382/145 |

FOREIGN PATENT DOCUMENTS

| | | |
|---|---|---|
| EP | 0 402 191 B1 | 12/1990 |
| EP | 0 601 580 A1 | 6/1994 |
| EP | 1 037 012 A1 | 9/2000 |
| JP | 0225038 | 12/1984 |
| JP | 11-211421 | 8/1999 |
| JP | 11-211422 | 8/1999 |
| SU | 1747877 A1 | 7/1992 |
| WO | WO 99/45340 | 9/1999 |
| WO | WO 01/84382 A1 | 11/2001 |
| WO | WO 02/25723 A2 | 3/2002 |
| WO | WO 02/27288 A1 | 4/2002 |
| WO | WO 02/50501 A1 | 6/2002 |
| WO | WO 02/065545 A2 | 8/2002 |
| WO | WO 02/069390 A2 | 9/2002 |
| WO | WO 02/079760 A2 | 10/2002 |
| WO | WO 02/084213 A1 | 10/2002 |
| WO | WO 03/071471 A1 | 8/2003 |
| WO | WO 2004/008068 A1 | 1/2004 |

OTHER PUBLICATIONS

Michaelis, A. et al., "Spectroscopic Anisotropy Micro-Ellipsometry (SAME) for determination of lateral and vertical dimensions of sub-micron lithographic structures" IEEE Catalog No. 99TH8453 (1999) pp. 131-134.

NanoWave:Technology/development tools, http://www.nanowave.com/technology_applications/tech_devtoolsPR.html, 2 pages, downloaded Apr. 9, 2002.

NanoWave:Technology/how it works, http://www.nanowave.com/technology_applications/tech_HIWPR.html, 3 pages, downloaded Apr. 9, 2002.

NanoWave:Technology/product design, http://www.nanowave.com/technology_applications/tech_designPR.html, 4 pages, downloaded Apr. 9, 2002.

"A Diffraction Grating Analysis Tool", downloaded May 7, 2001 from <http://www.gsolver.com/gsprod.html>, Grating Solve Development Co. (1999).

Ahmed, S., et al., "Comparison of beam propagation method and rigorous coupled-wave analysis for single and multiplexed volume gratings", Applied Optics, vol. 35, No. 22, Aug. 1, 1996, pp. 4426-4435.

Allgair, J. et al., "Implementation of Spectroscopic Critical Dimension (SCDTM) for Gate CD Control and Stepper Characterization", *Proceedings of SPIE*, vol. 4344 (2001), pp. 462-471.

Azzam, R. et al., "Ellipsometry And Polarized Light" *Elsevier Science Publishers* (1977, 1987) pp. 476-481.

Bao, G. et al., "Mathematical studies in rigorous grating theory", *J. Opt. Soc. Am. A*, vol. 12, No. 5 (1995), pp. 1029-1042.

Bao, G. et al., "Modeling and Optimal Design of Diffractive Optical Structures", pp. 1-27. (The correct site is Survey on Industrial Math. 8 (1998), 37-62).

Benson, T. et al., "In-situ Spectroscopic Reflectometry for Polycrystalline Silicon Thin Film Etch Rate Determination During Reactive Ion Etching", Dept. of Electrical Engineering & Computer Science an the Center for Display Technology & Manfuacturing, University of Michigan, pp. 1-34.

Bischoff J. et al., "Modeling of optical scatterometry with finite-number-of-periods gratings", *SPIE* vol. 3743 (1999) pp. 41-46.

Bischoff, J. et al., "Single feature metrology by means of light scatter analysis", *SPIE* vol. 3050 (1997) pp. 574-589.

Bishop, K. P. et al., "Grating line shape characterization using scatterometry", *SPIE*, vol. 1545 (1991) pp. 64-73.

Bishop, K. P. et al., "Use of scatterometry for resist process control", *Proc. SPIE—Int. Soc. Opt. Eng.*, vol. 1673 (1992) pp. 441-452.

Bosenberg, W. et al., "Linewidth Measurement on IC Wafers by Diffraction from Grating Test Patterns", *Solid State Technology*, vol. 26, No. 7 (1983) pp. 79-85.

Brauer, R. et al., "Eletromagnetic diffraction analysis of two-dimensional gratings", Optics Communications, vol. 100 (1993) pp. 1-5.

Chang, N. Y., et al., "Algorithm based on rigorous coupled-wave analysis for diffractive optical element design", J. Opt. Soc. Am. A, Opt. Image Sci. Vis. (USA), vol. 18, No. 10, Oct. 2001, pp. 2491-2501.

Chateau, N. et al., "Algorithm for the rigorous coupled-wave analysis of grating diffraction," *J. Opt. Soc. Am.* A, vol. 11 (1994), pp. 1321-1331.

Corle, T., et al., "Polarization-enhanced imaging of photoresist gratings in the real-time scanning optical microscope", *Applied Optics*, vol. 33, No. 4 (1994) pp. 670-677.

Coulombe, S. A. et al., "Modal characteristics of short-pitch photoresist gratings exhibiting zero-order diffraction anomalies", *J. Opt. Soc. Am. A*, vol. 16, No. 12 (Dec. 1999), pp. 2904-2913.

Coulombe, S. A. et al., "Scatterometry measurement of sub-0.1 μm linewidth gratings", *J. Vac. Sci. Technol.. B*, vol. 16, No. 1 (1998) pp. 80-87.

Coulombe, S. et al., "Ellipsometric-Scatterometry for sub-01. mm CD measurements" *SPIE* vol. 3332 (1988) pp. 282-292.

Damar, H. et al., "Diffraction Characterization for Process Monitoring, Linewidth Measurement and Alignment" *SPIE* vol. 470 (1984) pp. 157-163.

Davidson, M. et al., "A comparison between rigorous light scattering methods", *SPIE* vol. 3051 (1997) pp. 606-619.

Dong Hoon Lee, et al., "Analysis of topological effects of phase-shifting mask by boundary element method", J. Inst. Electron. Eng. Korea D (South Korea), vol. 36-D, No. 11, Nov. 1999, pp. 33-44.

Galarza, C. et al., "Real-time Estimation of Patterned Wafer Parameters Using In Situ Spectroscopic Ellipsometry", *Proceedings of the IEEE* (1999) pp. 773-778.

Gaspar, S. M. et al., "Laser scatterometry for process characterization", *AIP Conference Proceedings*, vol. 227, No. 1, (1991) pp. 54-55.

Gaylord, T. et al., "Analysis and Applications of Optical Diffraction by Gratings," *Proceedings of the IEEE*, vol. 73, (1984), pp. 894-937 (1985).

Glytsis, E. et al., "Rigorous Coupled-Wave Analysis And Applications Of Grating Diffraction", *Critical Reviews Of Optical Science and Technology*, vol. CR49 (1993), pp. 1-31.

Glytsis, E. et al., "Three-dimensional (vector) rigorous coupled-wave analysis of anisotropic grating diffraction", *J. Opt. Soc. Am. A*, vol. 7, No. 8 (1990), pp. 1399-1420.

Glytsis, E. N. et al., "Review of rigorous coupled-wave analysis and of homogeneous effective medium approximations for high spatial-frequency surface-relief", In NASA. Marshall Space Flight Center, Conference on Binary Optics: An Opportunity for Technical Exchange Feb. 23-25, 1993, p. 61-76.

Han, Chang-Wook, et al., "Rigorous coupled-wave analysis of antireflective surface-relief gratings" J. Opt. Soc. Korea (South Korea) vol. 1, No. 1, Mar. 1997, pp. 26-35.

Han, S. et al., "Electromagnetic scattering of two-dimensional surface-relief dielectric grating", *Applied Optics*, vol. 31 (1992) pp. 2343-2352.

Hatab, Ziad R. et al., "Sixteen-megabit dynamic random access memory trench depth characterization using two-dimensional diffraction analysis", *J. Vac. Sci. Technol. B*, vol. 13, No. 2 (1995) pp. 174-182.

Hauge, P., "Recent Developments in Instrumentation in Ellipsometry", Surface Science 96, (1980) pp. 108-140.

Haverlag, M. et al., "In situ ellipsometry and reflectometry during etching of patterned surfaces: Experiments and simulations", *Journal of Vacuum Science & Technology B*, vol. 10, No. 6 (1992) pp. 2412-2418.

Heimann, P. et al., "Optical Etch-Rate Monitoring: Computer Simulation of Reflectance", *Journal Electrochem. Soc.*, vol. 131, No. 4 (1984) pp. 881-885.

Henderson, G. N., "Semiconductor quantum electron wave transport, diffraction, and interference: analysis, device, and measurement", Dissertation Georgia Of Technology, vol. 54-10B, 1993, pp. 5312 209 page(s).

Hickman, K. C. et al., "Use of diffracted light from latent images to improve lithography control", *J. Vac. Sci. & Tech. B*, vol. 10, No. 5 (1992) pp. 2259-2266.

Huang, H. et al., "Normal-incidence spectroscopic ellipsometry for critical dimension monitoring", *Applied Physics Letters*, vol. 78 (2001) pp. 3983-3985.

Jarem, J. M., "Rigorous coupled wave analysis of radially and azimuthally-inhom- ogeneous, elliptical, cylindrical systems" (Abstract), J. Electromagn. Waves Appl. (Netherlands), vol. 15, No. 10, 2001, pp. 1367-1368.

Jarem, J. M., et al., "Rigorous coupled-wave analysis of photorefractive reflection gratings", J. Opt. Soc. Am. B, Opt. Phys. (USA) vol. 15, No. 7, Jul. 1998, pp. 2099-2106.

Jarem, J.M. "A rigorous coupled-wave analysis and crossed-diffraction grating analysis of radiation and scattering from three-dimensional inhomogeneous objects" IEEE Transactions on Antennas and Propagation, vol. 46, No. 5, May 1998, p. 740, 741.

Jiang Yongyuan, et al., Rigorous coupled wave analysis of dynamic diffraction properties of photorefractive phase grating Acta Photonica Sin. (China) vol. 29, No. 3, Mar. 2000, pp. 216-222.

Jiang Yongyuan, et al., "Rigorous coupled wave analysis of dynamic property of photorefractive anisotropic self-diffraction" Acta Photonica Sin. (China), vol. 29, No. 9, Sep. 2000, pp. 787-790.

Kamiya, N., "Rigorous coupled-wave analysis for practical planar dielectric gratings. 2. Diffraction by a surface-eroded hologram layer" Appl. Opt. (USA) vol. 37, No. 25, Sep. 1, 1998, pp. 5854-5863.

Kamiya, N., "Rigorous coupled-wave analysis for practical planar dielectric gratings. 3. Increase of higher-order lights owing to degenerated complex diffraction" Appl. Opt. (USA), vol. 37, No. 25, Sep. 1, 1998, pp. 5864-5878.

Kamiya, N., "Rigorous coupled-wave analysis for practical planar dielectric gratings. 1. Thickness-changed holograms and some characteristics of diffraction efficiency", Appl. Opt. (USA) vol. 37, No. 25, Sep. 1, 1998, pp. 5843-5853.

Kleinknecht, H. et al., "Linewidth measurement on IC masks and wafers by grating test patterns", *Applied Optics*, vol. 19, No. 4 (1980) pp. 525-533.

Kong, W. et al., "A Hybrid Analysis Ellipsometry Data from Patterned Structures" *Characterization and Metrology for ULSI Technology: 2000 International Conference*, pp. 373-377 (2001).

Kong, W. et al., "Analysis of Time-Evolved Spectroscopic Ellipsometry Data from Patterned Structures for Etching Process Monitoring and Control", Dept. of Electrical Engineering and Computer Science, University of Michigan, Four pages.

Kong, W., "Analysis of Spectroscopic Ellipsometry from Patterned Structures for Etching Process Monitoring and Control", Dissertation University of Michigan, 2001, 141 page(s).

Konstastantinos P. et al., "Use of Light Scattering in Characterizing Reactively Ion Etched Profiles", ATT&T Bell Laboratories, Murray Hill, NJ 07974, p. No. and date unavailable; Also cited in NAN007 RX as Giapis, K. et al., "Use of Light Scattering in Characterizing Reactively Ion Etched Profiles", J. Vac. Sci. Technol. A, vol. 9 (1981), pp. 664-668.

Krukar, R. et al., Overlay and Grating Line Shape Metrology Using Optical Scatterometry (unclassified) DARPA I 1993 Final Report, (Oct. 11, 1993) Thirty-six pages.

Krukar, R. et al., "Reactive ion etching profile and depth characterization using statistical and neural network analysis of light scattering data", *J. Appl. Phys.*, vol. 74, No. 6 (1993) pp. 3698-3706.

Krukar, R. H. et al., "Analyzing simulated and measured optical scatter for semiconductor process verification", *Proc. SPIE—Int. Soc. Opt. Eng.*, vol. 1907 (1993) pp. 238-249.

Krukar, R. H. et al., "Using scattered light modeling for semiconductor critical dimension metrology and calibration", *Proc. SPIE—Int. Soc. Opt. Eng.*, vol. 1926 (1993) pp. 60-71.

Krukar, R. H. et al., "Wafer examination and critical dimension estimation using scattered light" *Proc. SPIE—Int. Soc. Opt. Eng.*, vol. 1661 (1992) pp. 323-332.

Lee, M. et al., "Analysis of Reflectometry and Ellipsometry Data from Patterned Structures", *Characterization and Metrology for ULSI Technology*, (1998) pp. 331-334.

Lee, S. G., et al., "More stable algorithm for rigorous coupled wave analysis applied to topography simulation in optical lithography and its numerical implementation", Proc. SPIE—Int. Soc. Opt. Eng. (USA), vol. 2726, 1996, pp. 288-298.

Lochbihler, H. et al., "Characterization of highly conducting wire gratings using an electromagnetic theory of diffraction" *Optics Communications* 100 (1993) pp. 231-239.

Lochbihler, H. et al., "Charactization of x-ray transmission gratings" *Applied Optics*, vol. 31 (1992) pp. 964-971.

Logofatu, P. C. et al. "Identity of the cross-reflection coefficients for symmetric surface-relief gratings", *J. Opt. Soc. Am. A, Opt.* vol. 16 No. 5 (May 1999) pp. 1108-1114.

Logofatu, P. C. et al. "Measurement precision of optical scatterometry" , *Proceedings of SPIE*, vol. 4344 (2001), pp. 447-453.

Logofatu, P. C. et al. "Scatterometry: a metrology for subwavelength surface relief gratings", *Proceedings of SPIE*, vol. 4344 (2001), pp. 472-483.

Logofatu, P. C. et al., "Sensitivity analysis of fitting for scatterometry", *Proc. SPIE—Int. Soc. Opt. Eng.*, vol. 3677 (1999) pp. 177-183.

Logofatu, P.C., "Sensitivity-optimized scatterometry", Dissertation The University of New Mexico, vol. 61-11B, 2000, pp. 5942 181 page(s).

Lopez, A. G. "Reformulation of the rigorous coupled-wave analysis (RCWA) equations: Photonic crystals applications" Dissertation, Cornell University, vol. 61-04B, 2000, pp. 2113 136 pages.

Marx, D. et al., "Polarization quadrature measurement of subwavelength diffracting structures", *Applied Optics*, vol. 36, No. 25 (1997), pp. 6434-6440.

McNeil, J. R. "Application of optical scatterometry to microelectronics processing", *Technical Digest. Summaries of Papers Presented at the Conference on Lasers and Electro-Optics.*, vol. 6 (1998) pp. 348-349.

McNeil, J. R. et al., "Scatterometry applied to microelectronics", *Solid State Technol.*, vol. 36, No. 3 (1993) pp. 29-30.

McNeil, J. R., et al., "Scatterometry applied to microelectronics processing" *Solid State Technol.* vol. 36, No. 4 (1993) pp. 53-56.

McNeil, J. R., "Instrumentation to Enhance Optical Scatterometry for Semiconductor Metrology Development", Final Rept. Sep. 1, 1993-Feb. 28, 1998, Contract No. F49620-93-1-0512, Defense Technical Information Center (DTIC) order No. AD-354-189 (1998) (23 pages).

McNeill, J. et al., "Scatterometry Applied to Microelectronics Processing" *Microlithography World* (1992) pp. 16-22.

Mills, D. et al., "Spectral ellipsometry on patterned wafers," *SPIE*, vol. 2637 (1995) pp. 194-203.

Milner, L. M et a., "Latent image exposure monitor using scatterometry", *SPIE Proceedings*, vol. 1673 (1992), 10 pages.

Milner, L. M. et al., "Lithography process monitor using light diffracted from a latent image", *Proc. SPIE—Int. Opt. Eng.*, vol. 1926 (1993) pp. 94-105.

Minhas, B. K. et al., "Ellipsometric scatterometry for the metrology of sub-0.1- μm-linewidth structures", *Applied Optics*, vol. 37 No. 22 (Aug., 1998) pp. 5112-5115.

Minhas, B. K. et al., "Towards sub-0.1 mu m CD measurements using scatterometry", *Proc. SPIE—Int. Soc. Opt. Eng.*, vol. 2725 (1996) pp. 729-739.

Moharam, M. et al., "Diffraction analysis of dielectric surface-relief gratings", *J. Opt. Soc. Am.*, vol. 72 (1982) pp. 1385-1392.

Moharam, M. et al., "Diffraction characteristics of photoresist surface-relief gratings" *Applied Optics*, vol. 23 (1984) pp. 3214-3220.

Moharam, M. et al., "Formulation for stable and efficient implementation of the rigorous coupled-wave analysis of binary gratings", *J. Opt. Soc. Am.*, vol. 12 (1995) pp. 1068-1076.

Moharam, M. et al., "Rigorous coupled-wave analysis of planar-grating diffraction", *J. Opt. Soc. Am.*, vol. 71, No. 7 (1981) pp. 811-818.

Moharam, M. et al., "Stable implementation of the rigorous coupled-wave analysis for surface-relief gratings: enhanced transmittance matrix approach", *J. Opt. Soc Am.*, vol. 12 (1995) pp. 1077-1086.

Moharam, M. et al., "Three-dimensional vector coupled-wave analysis of planar-grating diffraction", *J. Opt. Soc. Am.*, vol. 73, No. 9 (1983), pp. 1105-1112.

Moharam, M., "Coupled-Wave Analysis of Two-Dimensional Dielectric Gratings", *SPIE* vol. 883 (1988) pp. 8-11.

Moharam, M.G. et al, "Rigorous Coupled-Wave Analysis of Grating Diffraction- E-mode polarization and losses", Jnl. of the Optical Society of America, vol. 73, No. 4, Apr. 83, p. 451-455.

Moharam, M.G. et al, "Rigorous coupled-wave analysis of metallic surface-relief gratings" Optical Society of America, Journal, A: Optics and Image Science Optical Society of America, Journal, A: Optics and Image Science, vol. 3, Nov. 1986, p. 1780-1787.

Murnane, M. R. et al., "Scatterometry for 0.24-0.70 um developed photoresist metrology", *SPIE*, vol. 2439 (1995) pp. 427-436.

Murnane, M. R. et al., "Subwavelength photoresist grating metrology using scatterometry", *Proc. SPIE—Int. Soc. Opt. Eng.*, vol. 2532 (1995) pp. 251-261.

Nakagawa, W., et al., "Analysis of near-field effects in artificial dielectric structures using rigorous coupled-wave analysis", Conference Proceedings—Lasers and Electro-Optics Society Annual Meeting-LEOS, vol. 2, 1999, p. 495-496.

Nakagawa, W., et al., "Ultrashort pulse propagation in near-field periodic diffractive structures by use of rigorous coupled-wave analysis", J. Opt. Soc. Am. A, Opt. Image Sci. Vis. (USA), vol. 18, No. 5, May 2001, pp. 1072-1081.

Naqvi, S. S. H. et al., "Etch depth estimation of large-period silicon gratings with multivariate calibration of rigorously simulated diffraction profiles", *J. Opt. Soc. Am. A*, vol. 11, No. 9 (1994) pp. 2485-2493.

Naqvi, S. S. H., et al., "Optical scatterometry for process metrology", *Optical metrology; Proceedings of the Conference*, (Jul. 1999) pp. 129-144.

Niu, X., et al., "Specular Spectroscopic Scatterometry", IEEE Transactions on Semiconductor Manufacturing, vol. 14, No. 2, May 2001, pp. 97-111.

Peng, Song, et al., "Efficient and stable implementation of rigorous coupled-wave analysis for surface-relief gratings", Proc. SPIE—Int. Soc. Opt. Eng. (USA), vol. 2532, 1995, pp. 475-480.

Peng, Song, et al., "Efficient implementation of rigorous coupled-wave analysis for surface-relief gratings", Journal of the Optical Society of America A: Optics and Image Science, and Vision, vol. 12, No. 5, May 1995, 1087-1096.

Press, W. et al., "Numerical Recipes: The Art of Scientific Computing,", *Cambridge University Press*, Section 14.4 (1986), pp. 521-528.

Prins, S. L. et al., "Scatterometric sensor for PEB process control", *Proc. SPIE—Int. Soc. Opt. Eng.*, vol. 2725 (1996) pp. 710-719.

Raymond, C. et al., "Metrology of subwavelength photoresist gratings using optical scatterometry" *J. Vac. Sci. Technology*. B 13 (1995) pp. 1484-1495.

Raymond, C. et al., "Resist and etched line profile characterization using scatterometry" SPIE vol. 3050 (1977) 476-486.

Raymond, C. et al., "Scatterometry for the measurement of metal features" *Proceedings of SPIE* vol. 2998 (2000) pp. 135-146.

Raymond, C. J. et al., "Multiparameter CD measurements using scatterometry", *Proc. SPIE—Int. Soc. Opt. Eng.*, vol. 2725 (1996) pp. 698-709.

Raymond, C. J. et al., "Multiparameter grating metrology using optical scatterometry" *J. of Vac. Sci. Tech. B*, vol. 15, No. 2 (1997) pp. 361-368.

Raymond, C. J. et al., "Multi-parameter process metrology using scatterometry", *Proc. SPIE—Int. Soc. Opt. Eng.*, vol. 2638 (1995) pp. 84-93.

Raymond, C. J. et al., "Resist and Etched line profile characterization using scatterometry", *Proc. SPIE—Int. Soc. Opt. Eng.*, vol. 3050 (1997) pp. 476-486.

Raymond, C. J. et al., "Scatterometry for CD measurements of etched structures", *Proc. SPIE—Int. Soc. Opt. Eng.*, vol. 2725 (1996) pp. 720-728.

Sohail, S. "A simple technique for linewidth measurement of gratings on photomasks", *Proc. SPIE—Int. Soc. Opt. Eng.*, vol. 1261 (1990) pp. 495-504.

Sohail, S. et al. "Grating parameter estimation using scatterometry" *Proc. SPIE—Int.Soc. Opt. Eng.*, vol. 1992 (1993) pp. 170-180.

Sohail, S. et al., "Diffractive techniques for lithographic process monitoring and control", *J. Vac. Sci. Technol. B*, vol. 12, No. 6 (1994) pp. 3600-3606.

Sohail, S. et al., "Linewidth measurement of gratings on photomasks: a simple technique", *Applied Optics*, vol. 31, No. 10 (1992) pp. 1377-1384.

Stover, J. C., et al., "Modeled and measured scatter from vias", SPIE Conf. on Surface Characterization of Computer Disks, Wafers, and Flat Panel Displays, Jan. 1999, pp. 65-71.

Sun, J. et al., "Profile Measurement on IC Wafers by Holographic Interference", *SPIE* vol. 673 (1986) pp. 135-143.

Tadros, K., "Understanding metrology of polysilicon gates through reflectance measurements and simulation", *SPIE* vol. 1464 (1991) pp. 177-186.

Tu, K. et al., "Multiple-scattering theory of wave diffraction by superposed volume gratings", *J. Opt. Soc. Am. A.*, vol. 7, No. 8 (1990), pp. 1421-1435.

Wilson, S. M. G. et al., "Phase shift mask metrology using scatterometry", *Proc. SPIE—Int. Soc. Opt. Eng.*, vol. 2322 (1994) pp. 305-315.

Yeung, M., et al., "Electromagnetic Scatterometry Applied to In Situ Metrology", *Proceedings of SPIE*, vol. 4344 (2001), pp. 484-495.

Ziger, D. et al., "Linesize effects on ultraviolet reflectance spectra", *Society of Photo-Optical Instrumentation Engineers* (1997), Paper 37046.

Zylberberg, Z. et al., "Rigorous coupled-wave analysis of pure reflection gratings" Optical Society of America, Journal, vol. 73, Mar. 1983, p. 392-398.

* cited by examiner

SPECTROSCOPICALLY MEASURED OVERLAY TARGET

BACKGROUND OF THE INVENTION

1. Field of the Invention

The present invention relates to overlay metrology, and in particular to an overlay target that can be accurately measured spectroscopically.

2. Discussion of the Related Art

Semiconductor processing for forming integrated circuits requires a series of processing steps. These processing steps include the deposition and patterning of material layers such as insulating layers, polysilicon layers, and metal layers. The material layers are typically patterned using a photoresist layer that is patterned over the material layer using a photomask or reticle. Typically the photomask has alignment targets or keys that are aligned to fiduciary marks formed in the previous layer on the substrate. However, as the integrated circuit feature sizes continue to decrease to provide increasing circuit density, it becomes increasingly difficult to measure the alignment accuracy of one masking level to the previous level. This overlay metrology problem becomes particularly difficult at submicrometer feature sizes where overlay alignment tolerances are reduced to provide reliable semiconductor devices.

FIGS. 1A and 1B show conventional overlay targets used with conventional imaging metrology methods. FIG. 1A shows a typical Box-in-Box overlay target 2. Target 2 is formed by producing an etched box 4 in a material layer 6 on a substrate. A corresponding smaller box 8 on the photomask or reticle is aligned to the larger box 4 so that the centers of the large and small boxes are aligned.

FIG. 1B shows a Bar-in-Bar overlay target 12, which is similar to target 2 shown in FIG. 1A. Target 12 is produced by etching bars 14 in a material layer 16 on a substrate. The bars 18 on the photomask are aligned to the overlay target alignment bars 14.

After the smaller box 8 or bars 18 are developed, i.e., exposed and etched, the overlay target is imaged to determine whether the photomask or reticle was properly aligned with the underlying layer. Conventionally, high magnification imaging is used to measure overlay alignment. Conventional imaging devices, unfortunately, suffer from disadvantages such as sensitivity to vibration and cost. Moreover, conventional imaging devices suffer from a tradeoff between depth-of-focus and optical resolution. Additionally, edge-detection algorithms used to analyze images for the purpose of extracting overlay error are inaccurate when the imaged target is inherently low-contrast or when the target suffers from asymmetries due to wafer processing.

Thus, there is a need in the semiconductor industry for improved overlay target metrology.

SUMMARY

An overlay target is measured spectroscopically in accordance with an embodiment of the present invention. Because spectroscopy is used, problems associated with high magnification optical measurement tools are avoided.

In accordance with one embodiment, the overlay target includes a first symmetrical diffraction grating on a first layer that is disposed over a substrate and a second symmetrical diffraction grating on a second layer that is disposed over the first symmetrical diffraction grating. The two diffraction gratings may be asymmetrical relative to each other. Thus, for example, there may be an offset phase shift between the two gratings, or the pitches or line widths of the two gratings may differ. In one embodiment, the gratings are diffraction gratings having parallel lines, where the two gratings have lines that are substantially parallel to each other. The overlay target may include additional symmetrical diffraction gratings, having lines that are perpendicular to the first and second symmetrical diffraction gratings. The asymmetry of the two diffraction gratings advantageously increases the resolution of mis-registration as well as provides the ability to accurately determine the direction of mis-registration.

In accordance with another embodiment of the present invention, a method of measuring the lateral alignment of one layer to an underlying layer includes providing a sample having an overlay target for measuring layer-to-layer alignment; and spectroscopically measuring the overlay target. Spectroscopically measuring the overlay target may include producing light that is incident on the overlay target, detecting light that is diffracted from the overlay target, constructing an optical model of the overlay target, calculating the diffracted light from the optical model of the overlay target, comparing the calculated diffracted light with the detected light that is diffracted from the overlay target, adjusting variable parameters in the optical model of the overlay target, recalculating the diffracted light from the optical model of the overlay target, comparing the recalculated diffracted light with the detected light that is diffracted from said overlay target, and repeating until an adequate fit between the calculated diffracted light and the detected light is found. In another embodiment, the detected light that is diffracted from the overlay target is compared with a library of diffracted light to determine the overlay error.

In another aspect of the present invention, the overlay target is optimized for measurement by modeling the overlay target. The overlay target may be optimized by generating a model of the overlay target using fixed parameters and at least one variable parameter and calculating the diffracted light signature for the model of the overlay target for a plurality of values of the variable parameter. Based on the diffracted light signature the optimized value of the variable parameter may be determined. In addition, the sensitivity of the model may be calculated based on the diffracted light signature and the optimized value of the variable parameter is determined using the calculated sensitivity. The optimization may be done for a single wavelength or a plurality of wavelengths of light. In one embodiment, the overlay target is optimized for measurement by generating a model of the overlay target using fixed parameters and at least one initial variable parameter; calculating the reflectance of the model with the initial variable parameter; adjusting the variable parameter; calculating the reflectance of the model with the adjusted variable parameter; calculating the sensitivity relative to the variable parameter; repeating the process for a plurality of values of the variable parameter; and determining at least one optimized value for the variable parameter using the calculated sensitivities. The variable parameter may be, e.g., the offset phase. Other variable parameters, such as pitch and line width, may also be optimized.

In another aspect of the present invention, an apparatus for spectroscopically measuring the lateral alignment of layers on a substrate by way of an overlay target composed of overlaying diffraction gratings includes a light source for producing broadband light to be incident on the overlay target and a light detector for spectroscopically detecting light that is diffracted from the overlay target. In addition, the apparatus includes a computer and a computer-usable medium having computer-readable program code embodied therein for causing the computer to determine a lateral overlay error based on the light that is diffracted from the overlay target. The code embodied in the computer-usable medium can cause the computer to perform the steps of constructing an optical model of the overlay target, calculating the diffracted light from the optical model of the overlay target, comparing the calculated diffracted light with the detected light that is diffracted from the overlay target, adjusting variable parameters in the optical model of the overlay target, recalculating the diffracted light from the optical model of the overlay target, comparing the recalculated diffracted light with the detected light that is diffracted from the overlay target, and repeating until an adequate fit between the calculated diffracted light and the detected light is found. Alternatively, the code embodied in the computer-usable medium can cause the computer to perform the steps of comparing the detected light that is diffracted from the overlay target with a library of diffracted light to determine the overlay error.

DETAILED DESCRIPTION

In accordance with an embodiment of the present invention, an overlay target is spectroscopically measured, which advantageously avoids problems associated with high magnification. In one embodiment, the overlay target is asymmetrical, which advantageously increases sensitivity in the spectroscopic measurement. Additionally, the overlay target can be optimized for sensitivity.

Figure 1A:
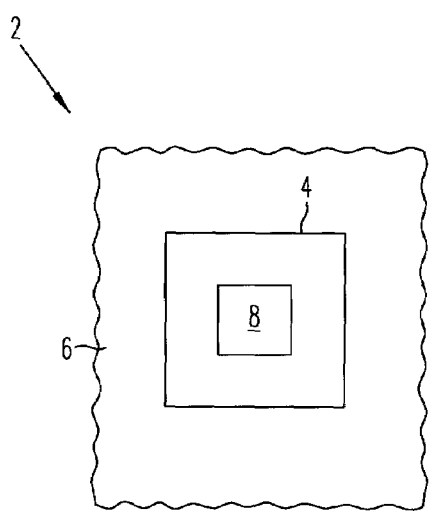
FIGS. 1A and 1B show conventional overlay targets, Box-in-Box and Bar-in-Bar, respectively, used with conventional imaging metrology methods.
Figure 1B:
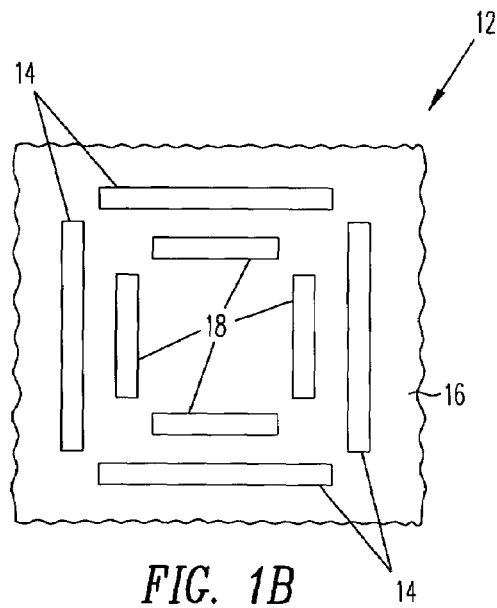
Figure 2:
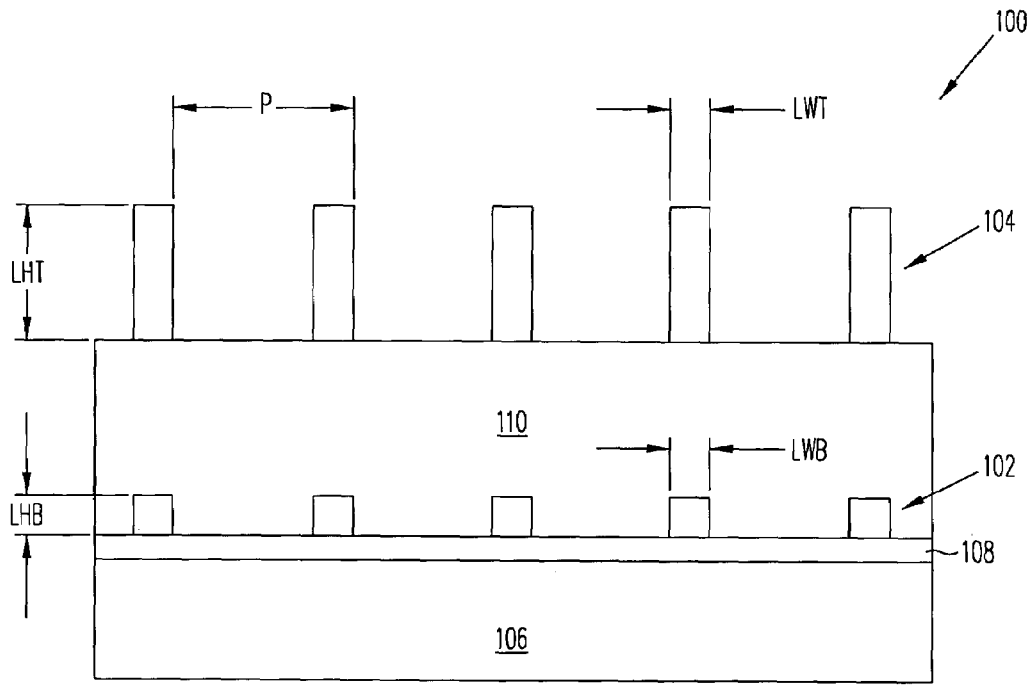
FIG. 2 shows a cross sectional view of an overlay target that includes two diffraction gratings in accordance with an embodiment of the present invention.

FIG. 2 shows a cross sectional view of an overlay target 100 in accordance with an embodiment of the present invention. Overlay target 100 includes two sets of diffraction grating structures; a bottom diffraction grating 102 and a top diffraction grating 104. Overlay target 100 is produced on a substrate 106, which is e.g., a silicon substrate, and any overlying layers, shown as layer 108, which may be a gate oxide layer, which is e.g., 3.5 nm thick. The bottom diffraction grating 102 is produced, for example, by producing a layer of appropriate material, such as a 200 nm layer of polysilicon, followed by a layer of photoresist. The desired image including the diffraction grating 102 is exposed in the photoresist, which is then developed. The polysilicon is then etched away leaving diffraction grating 102. Diffraction grating 102 may have a line width (LWB) of 200 nm, a line height (LHB) of 200 nm and a pitch (P) of 600 nm. The remaining photoresist is removed.

An overlying layer 110, which may be, e.g., a 1000 nm layer of silicon oxide, is deposited over diffraction grating 102. The top diffraction grating 104 is then produced using, e.g., photoresist, in a manner similar to the bottom diffraction grating 102, where the top diffraction grating 104 is separated from the bottom diffraction grating 102 by the thickness (THK) of layer 110, e.g., 1000 nm. For example, an 800 nm layer of the photoresist is deposited over layer 110. The desired image including the diffraction grating 104 is exposed in the photoresist layer. The photoresist is then developed, thereby leaving diffraction grating 104. Diffraction grating 104 may have a line width (LWT) of 200 nm, a line height (LHT) of 800 nm and a pitch (P) of 600 nm. It should be understood that the overlay target 100 may be produced using various materials and dimensions. For example, the dimensions of overlay target 100 may be altered to maximize sensitivity based on the types of materials used.

Figure 3A:
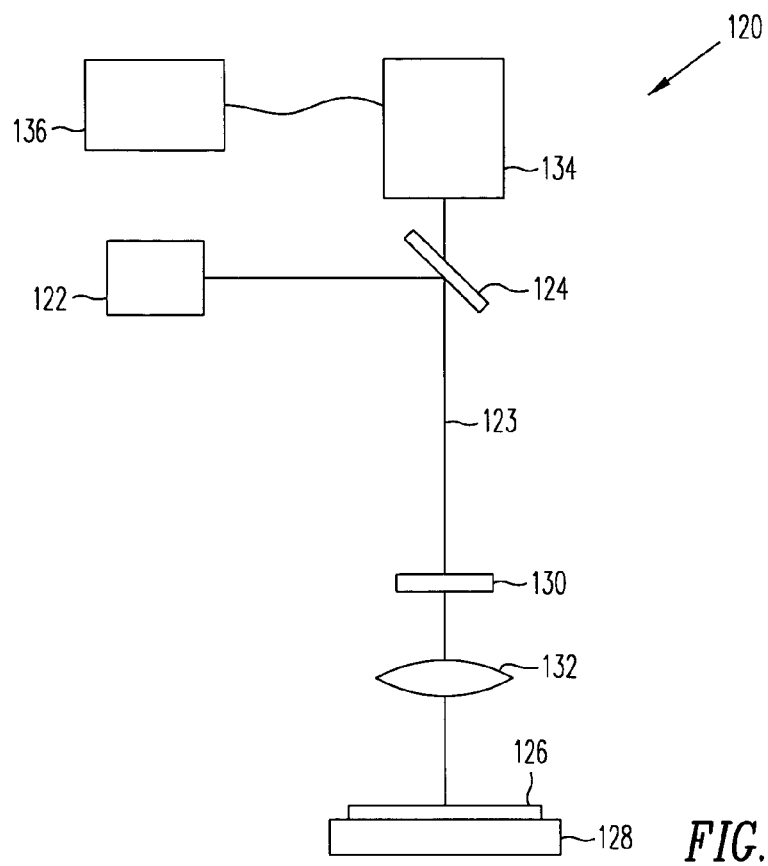
FIGS. 3A, 3B, and 3C are block diagrams showing a normal incidence polarized reflectance spectrometer an ellipsometer and a spectroscopic scatterometer, respectively, that may be used to spectroscopically measure the overlay target of FIG. 2.

FIG. 3A is a block diagram showing a normal incidence polarized reflectance spectrometer 120 that may be used to spectroscopically measure overlay target 100.

Spectrometer 120 is discussed in detail in the U.S. patent application entitled "Apparatus and Method for the Measurement of Diffracting Structures," filed Sep. 25, 2000, having Ser. No. 09/670,000, and the U.S. patent application entitled "Measurement Of Diffracting Structures Using One-Half Of The Non-Zero Diffracted Orders" filed Apr. 27, 2000, having Ser. No. 09/844,559, both of which have the same assignee as the present disclosure and are incorporated herein by reference. Spectrometer 120 may use rigorous coupled wave (RCW) analysis as described in Ser. No. 09/670,000, or folded rigorous coupled wave analysis as described in Ser. No. 09/844,559 to measure overlay target 100.

As shown in FIG. 3A, spectrometer 100 includes a polychromatic light source 122 that generates a light beam that is partially reflected by beam splitter 124 along the optical axis 123. The light beam is directed towards a sample 126 having an overlay target, such as target 100, to be measured. Sample 126 may be, e.g., a semiconductor wafer or flat panel display or any other substrate, and is supported by a stage 128, which may be a polar coordinate, i.e., R-θ, stage or an x-y translation stage. Spectrometer 120 includes a rotatable polarizer 130 and a lens 132 (or series of lenses) to polarize and focus the light beam onto the sample 126 at normal incidence. The beam is reflected off sample 126 and the reflected light is transmitted through lens 132 and polarizer 130. A portion of the reflected light is transmitted through beam splitter 124 and is received by a spectrophotometer 134. Spectrophotometer 134 is coupled to processor 136, which analyzes the data provided by spectrophotometer 134. Processor 136 is e.g., a computer with a computer-usable medium having computer-readable program code embodied therein for causing the computer to determine the overlay error based on the light that is diffracted from the overlay target. For more information on the general operation of a normal incidence polarized reflectance spectrometer, the reader is referred to Ser. Nos. 09/670,000 and 09/844,559, which are incorporated herein by reference.

Figure 3B:
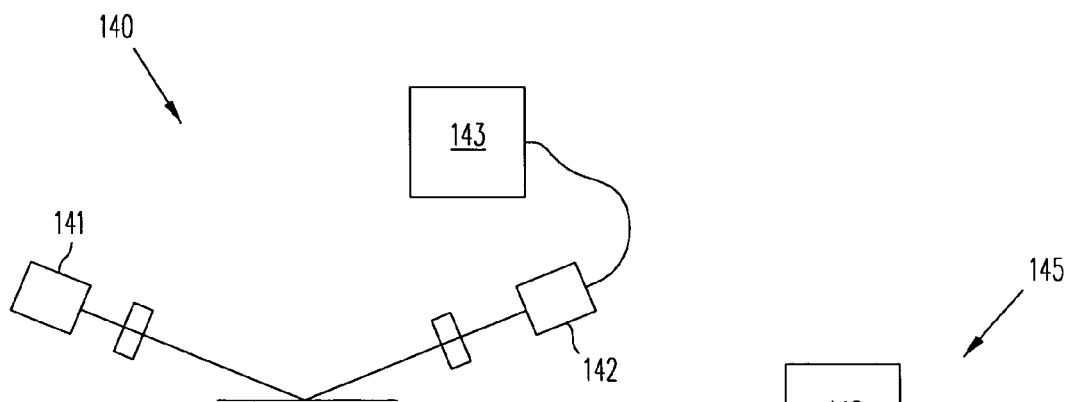
Figure 3C:
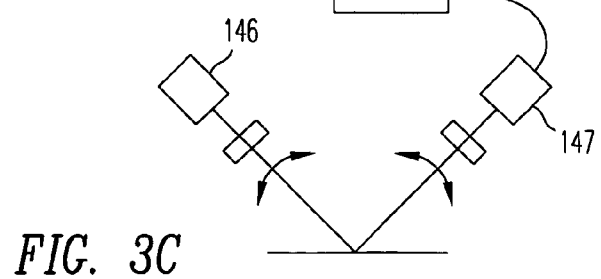

If desired, other measurement routines may be used to spectroscopically measure overlay target 100 including ellipsometry and scatterometry. FIGS. 3B and 3C show block diagrams of a spectroscopic ellipsometer 140 and spectroscopic scatterometer 145. Ellipsometer 140 includes a broadband radiation source 141 and a spectrophotometer 142, which is connected to a processor 143. Spectroscopic scatterometer 145 includes a broadband radiation source 146 and a spectrophotometer 147, which is connected to a processor 148. As indicated by the arrows in FIG. 3C, one or both of broadband radiation source 146 and spectrophotometer 147 are adjustable to alter the angle of incidence. The operation of an ellipsometer 140 and spectroscopic scatterometer 145 is well known to those skilled in the art. Processor 143 and 148 may be similar to processor 136 shown in FIG. 3A.

Figure 4:
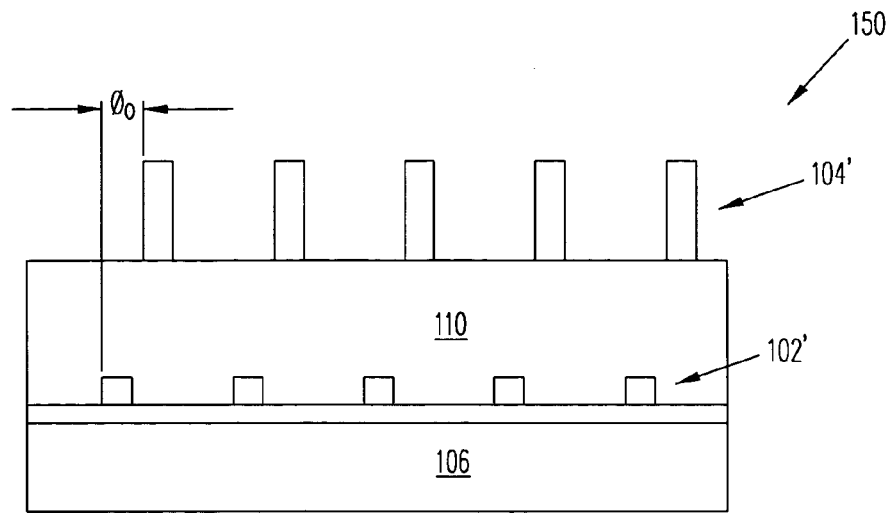
FIG. 4 shows another embodiment of the overlay target having an asymmetry, in the form of an offset phase between the top and bottom diffraction gratings.

It has been determined that because of the symmetry of the overlay target 100 shown in FIG. 2, the sensitivity of the spectral measurement is reduced particularly in terms of the direction of misalignment, i.e., whether the top diffraction grating is misaligned with the bottom diffraction grating to the right or left. Accordingly, in accordance with an embodiment of the present invention, an asymmetric overlay target is used. FIG. 4 shows an asymmetric overlay target 150 in accordance with an embodiment of the present invention. As shown in FIG. 4, asymmetric overlay target 150 is similar to overlay target 100 shown in FIG. 2, but with top diffraction grating 104' having an offset phase $\phi_0$ with respect to the bottom diffraction grating 102'. The overlay error is then determined by measuring the overall phase shift and subtracting the offset phase $\phi_0$.

The sensitivity of the overlay target to overlay error, i.e., shifts in phase between the top diffraction grating and the bottom diffraction grating, is a function of the process independent variables: specifically, the wavelength of impinging light, offset phase, top line-width, bottom line-width, pitch, and can be written in functional notation as $S(\lambda, \phi, LWT, LWB, P)$. It should be noted that while the process-independent variables are free for the target designer to specify, these variables are still subject to slight variations due to imperfections in pattern transfer. Other parameters, such as top grating height, bottom grating height, and sub-layer thickness are constrained by device specific requirements for the material parameters of the layers being measured. Therefore, designing a diffracting overlay target includes optimizing one or more of the process independent parameters, named above, to maximize the sensitivity of the overlay target to overlay error. Overlay error is defined for this particular target design as the difference between the nominal and measured relative grating shift. Thus the sensitivity is maximized when small variations in the relative grating shift produce large variations in the measured spectrum, which suggests the functional definition for the sensitivity function as the partial derivative of the measured spectrum with respect to the relative grating shift, as shown in the following equation:

$$S(\lambda_i, \varphi_j)LWT, LWB, P = \frac{|R(\lambda_i, \varphi_j)LWT, LWB, P - R(\lambda_i, \varphi_{j-1})LWT, LWB, P|}{\varphi_j - \varphi_{j-1}} \qquad \text{eq. 1}$$

$$= \frac{\partial R}{\partial \varphi}\bigg|_{\lambda_i, \varphi_j, LWT, LWB, P}$$

where $R(\lambda_1, \phi_j)$ is the calculated reflectance at a particular relative grating shift for a particular wavelength and $R(\lambda_1, \phi_{j-1})$ is the calculated reflectance at the previous relative grating shift at the same wavelength, and the sensitivity $S(\lambda_i, \phi_j)$ is in arbitrary units ranging from 0 to 14.

Note that the sensitivity is calculated for set values of the process independent variables: top line-width (LWT), bottom line-width (LWB), and pitch (P). In addition, while the sensitivity function must be maximized for small variations in relative grating shift, it must be minimized with respect to the other process-independent variables to avoid correlations between slight process-induced variations with the relative phase-shift. Numerical methods for maximizing and minimizing functions with respect to free variables are well known to those skilled in the art and can be accomplished, e.g., using the Levenberg-Marquardt non-linear regression method. The measured spectrum can be polarized reflectance with transverse electric polarization ($R_{TE}$), or polarized reflectance with transverse magnetic polarization ($R_{TM}$), or the ellipsometric variable $\Delta(\lambda)$, or the ellipsometric variable $\lambda(\Delta)$ or both $\Delta(\lambda)$ and $\lambda(\Delta)$. Here we optimize the spectral variations in the polarized reflectance spectrum as measured, e.g., by the spectrometer in FIG. 3A, which has the capability of measuring $R_{TE}$ and $R_{TM}$ as well as $\Delta$ and $\psi$.

For reference:

$$(\tan\Psi)e^{i\Delta} = \frac{R_p}{R_s} \qquad \text{eq. 2}$$

where $R_p$ and $R_s$ are the complex total reflection coefficients for p-polarized and s-polarized light and is well known to those skilled in the art.

Figure 5:
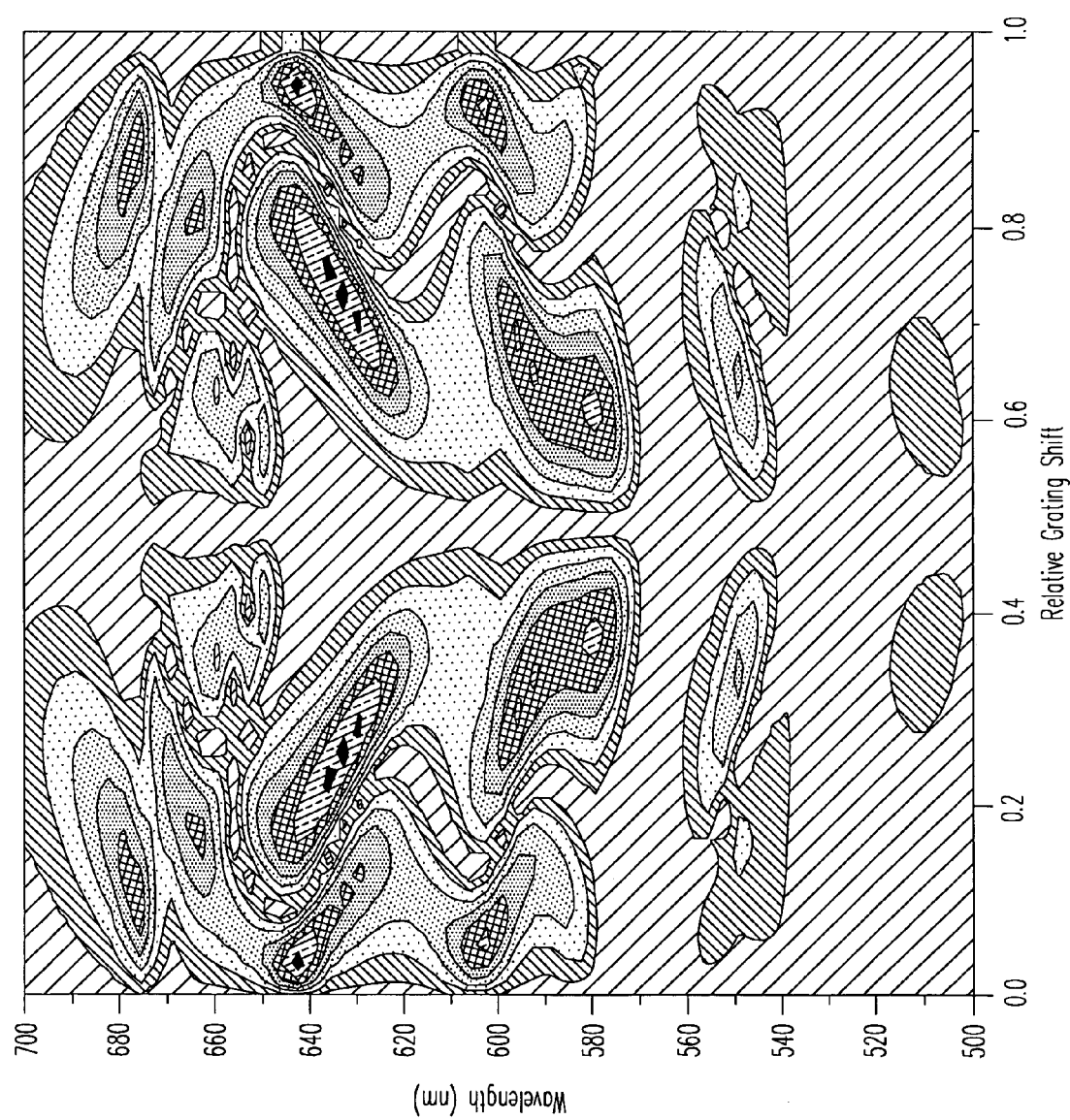
FIG. 5 is a sensitivity map showing the sensitivity of each wavelength to a relative grating shift

FIG. 5 is a sensitivity map showing the sensitivity of each wavelength to a relative grating shift, where the x axis shows the relative grating shift of the diffraction gratings from 0 to 1 and the y axis is the wavelength of light from 500 nm to 700 nm. The sensitivity of each wavelength of light for each relative grating shift was calculated using equation 1. As can be seen in FIG. 5, the sensitivity of the overlay target 150 is symmetrical about 0 and about 0.5, which correspond to perfect alignment between the top diffraction grating 104' and bottom diffraction grating 102' and a shift of 50% of the pitch, respectively.

Figure 6:
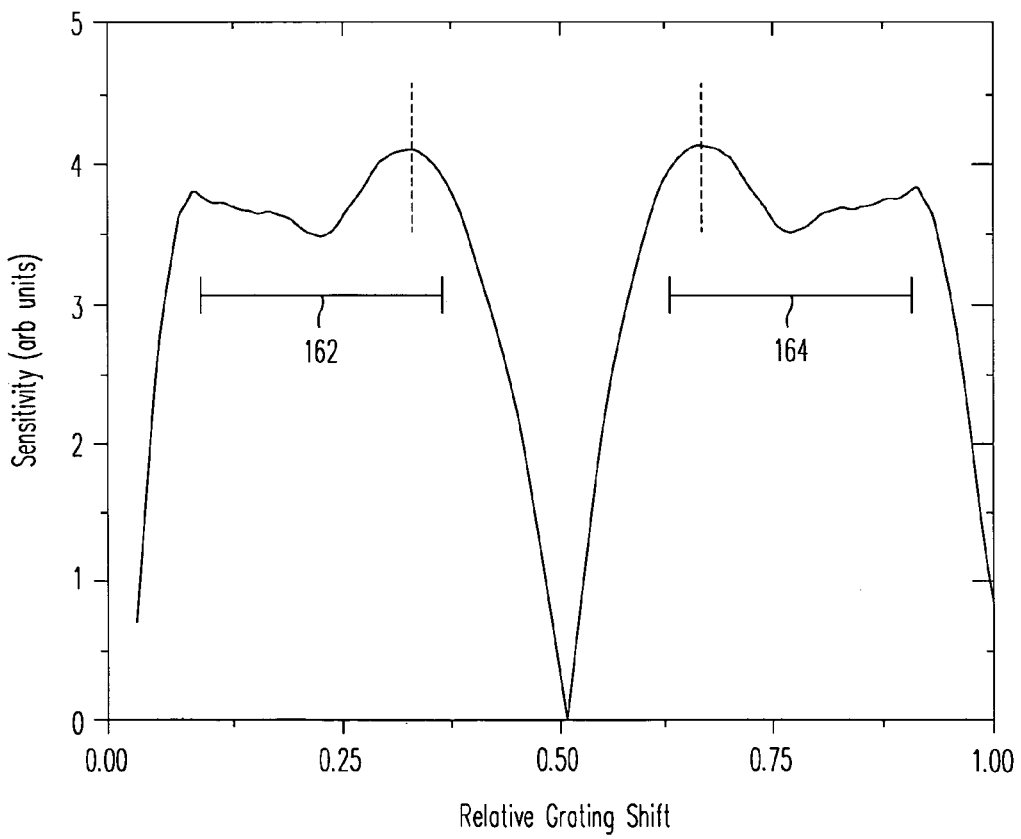
FIG. 6 is a graph showing the optimum offset phase for overlay sensitivity.

FIG. 6 is a graph showing the optimum grating shift, i.e., offset phase, for overlay sensitivity, where the x axis is the relative grating shift and the y axis is the sensitivity in arbitrary units. The sensitivity for each grating shift was averaged over the wavelength variable according to the following equation:

$$\langle S(\varphi) \rangle_\lambda = \frac{1}{N} \sum_{i=1}^{N} S(\lambda_i, \varphi) \qquad \text{eq. 3}$$

where N is the number of discrete wavelengths comprising the sensitivity spectrum. The slight shift of the curves in FIG. 6 to the right on the x axis is due the comparison of the reflectance for a current grating shift with the previous grating shift in equation 1. As can be seen in FIG. 6, maximum sensitivity lies between approximately 5% to 40% (and 60% to 95%) of the pitch P, indicated by bar 162 (and bar 164). While the maximum of the curves appears at approximately 34% and 66% of the pitch, there is a roll off between approximately 40% and 60%. Moreover, from inspection of the sensitivity map of FIG. 5 it can be seen that the various wavelengths are less sensitive to change when the relative grating shift is close to 50%. Accordingly, overlay target 150 may use an offset phase shift $\phi_0$ of approximately 25% (or 75%) of pitch P, which is approximately the center of bar 162, to provide adequate sensitivity. Thus, while any offset phase shift $\phi_0$ may be used to provide the desired asymmetry, an offset phase shift $\phi_0$ of approximately plus or minus 8% to 38% of the pitch P has been found to provide good results.

Figure 7A:
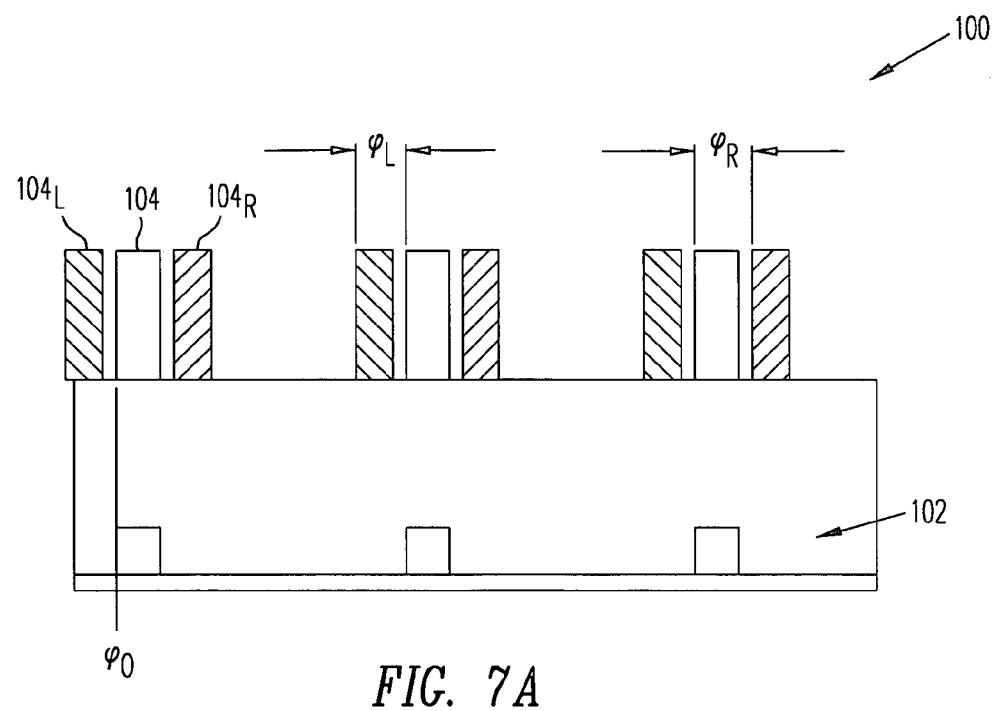
FIG. 7A shows a cross sectional view of overlay target with no offset phase shift and with a mis-registration to the left and right.
Figure 7B:
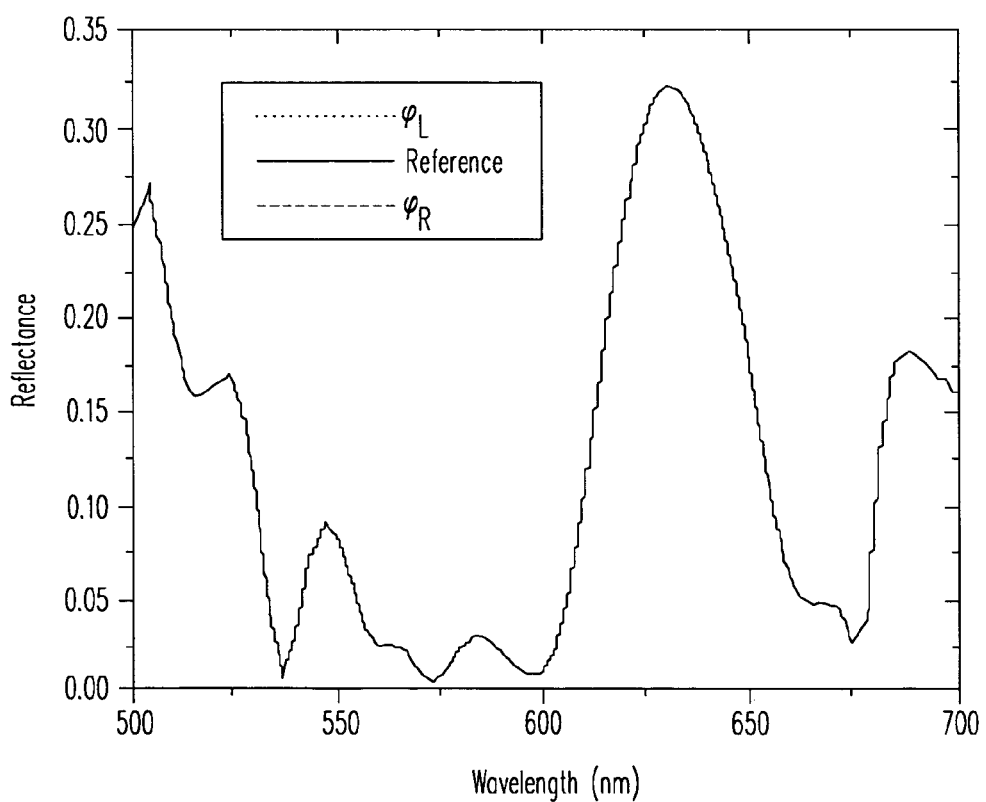
FIG. 7B is a graph of the reflectance with respect to wavelength for the overlay target shown in FIG. 7A.

FIG. 7A shows a cross sectional view of overlay target 100 with an offset phase shift $\phi_0$ of zero and a mis-registration to the left (illustrated by top diffraction gratings $104_L$, having phase shift $\phi_L$) and to the right (illustrated by top diffraction grating $104_R$ having phase shift $\phi_R$). FIG. 7B is a graph of the reflectance with respect to wavelength for overlay target 100 where the top diffraction grating 104 is in the reference position and where there is a phase shift of $\phi_R$ and $\phi_L$. As can be seen in FIG. 7B, with an overlay target with a zero offset phase shift $\phi_0$, any mis-registration, whether it is to the right or left, is difficult to detect. Moreover, the direction of mis-registration, i.e., to the left or right, is difficult to detect.

Figure 8A:
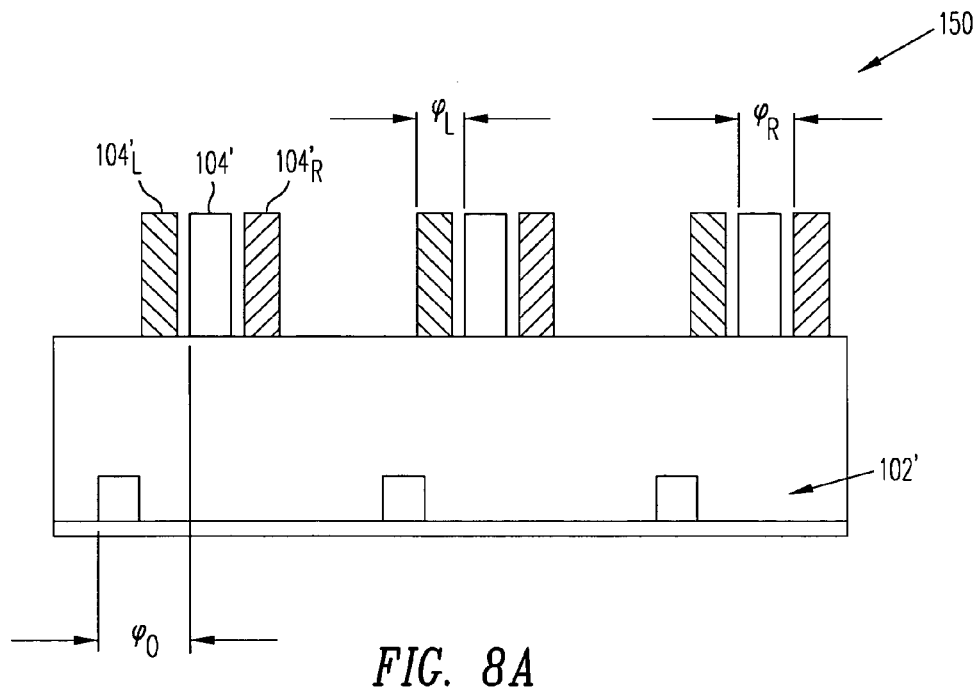
FIG. 8A shows a cross sectional view of an overlay target with an offset phase shift and with a mis-registration to the left and to the right.
Figure 8B:
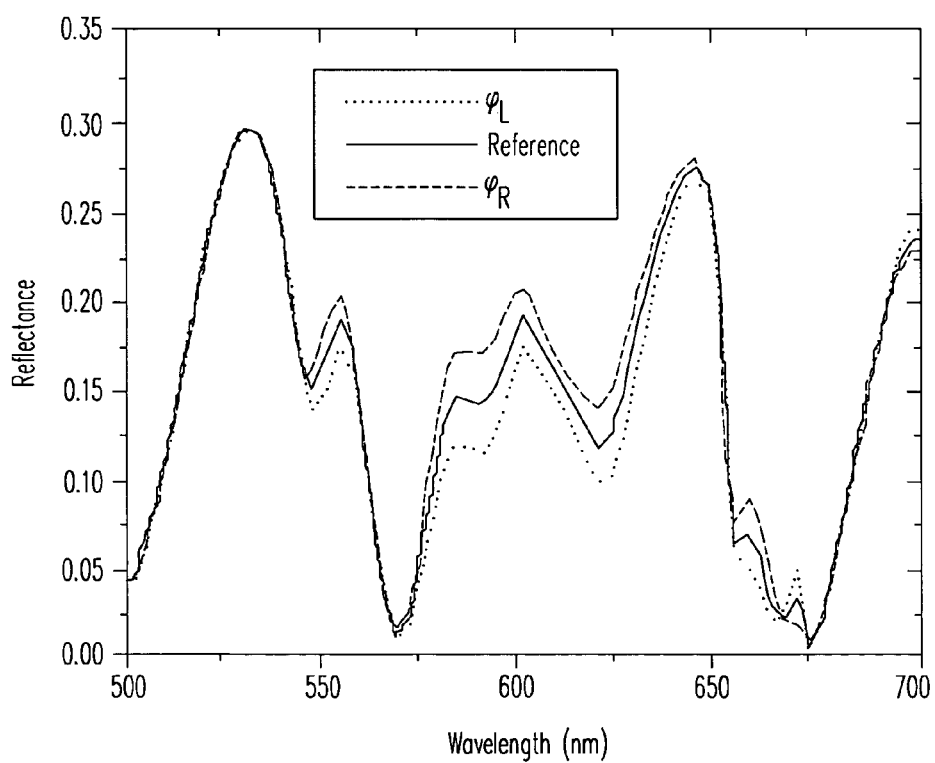
FIG. 8B is a graph of the reflectance with respect to wavelength for the overlay target shown in FIG. 8A.

FIG. 8A shows a cross sectional view of overlay target 150 with a non-zero offset phase $\phi_0$ of the top diffraction grating 104'. Similar to FIG. 7A, FIG. 8A shows a mis-registration to the left (illustrated by top diffraction gratings $104'_L$ having phase shift ($\phi_L$) and to the right (illustrated by top diffraction grating $104'_R$ having phase shift $\phi_R$). FIG. 8B is a graph of the reflectance with respect to wavelength for overlay target 150 where the top diffraction grating 104' is in the reference position and where there is a phase shift of $\phi_R$ and $\phi_L$. As can be seen in FIG. 8B, the presence and direction of mis-registration of an asymmetrical overlay target, i.e., where there is a non-zero offset phase shift $\phi_0$, is easily detected.

Figure 9:
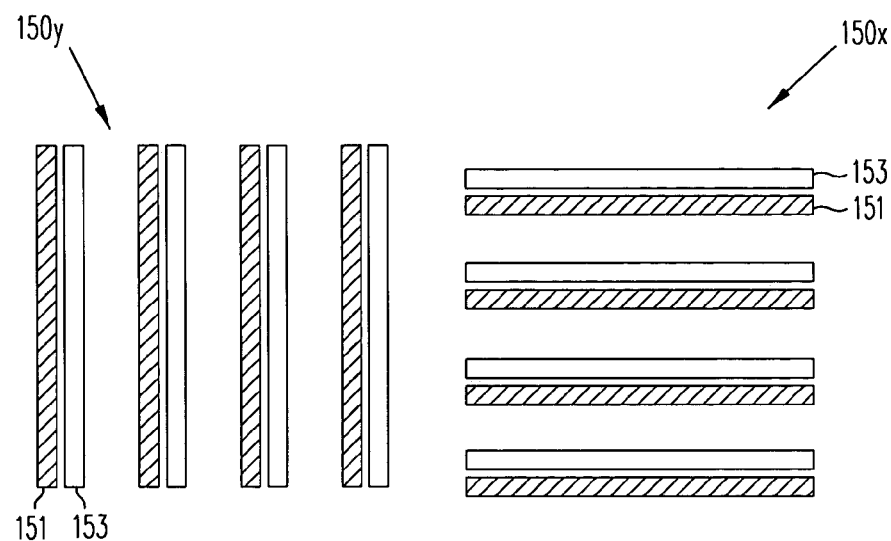
FIG. 9 shows the top view of two perpendicular overlay targets that may be used to measure mis-registration in both the x and y directions.

The overlay target 150 is sensitive to mis-registration in the direction perpendicular to the lines of the diffraction grating. Accordingly, two separate and perpendicular overlay targets are used to measure any mis-registration in the x and y directions. FIG. 9 shows the top view of two perpendicular overlay targets 150x and 150y that may be used to measure mis-registration in both the x and y directions, respectively, where the shaded lines 151 represent the bottom diffraction grating and the empty lines 153 represent the top diffraction grating.

Figure 10:
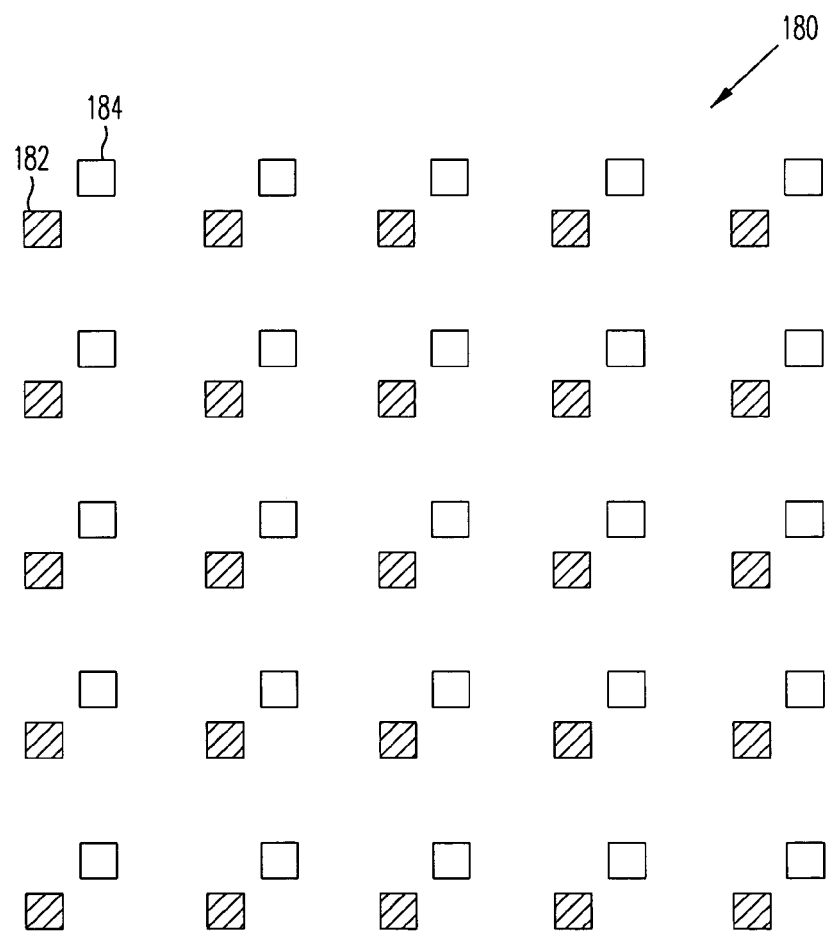
FIG. 10 is a top view of a two-dimensional overlay target in accordance with another embodiment of the present invention.

FIG. 10 is a top view of a two-dimensional overlay target 180, where the shaded targets 182 are on the bottom layer and the clear targets 184 are on the top layer. Two-dimensional overlay target 180 permits simultaneous measurement of x and y mis-registration. Two-dimensional overlay target 180 is shown in FIG. 10 as being asymmetric in both the x and y direction. It should be understood, however, that if desired, two-dimensional overlay target 180 may be asymmetrical in only the x or y direction or may be symmetrical.

Figure 11:
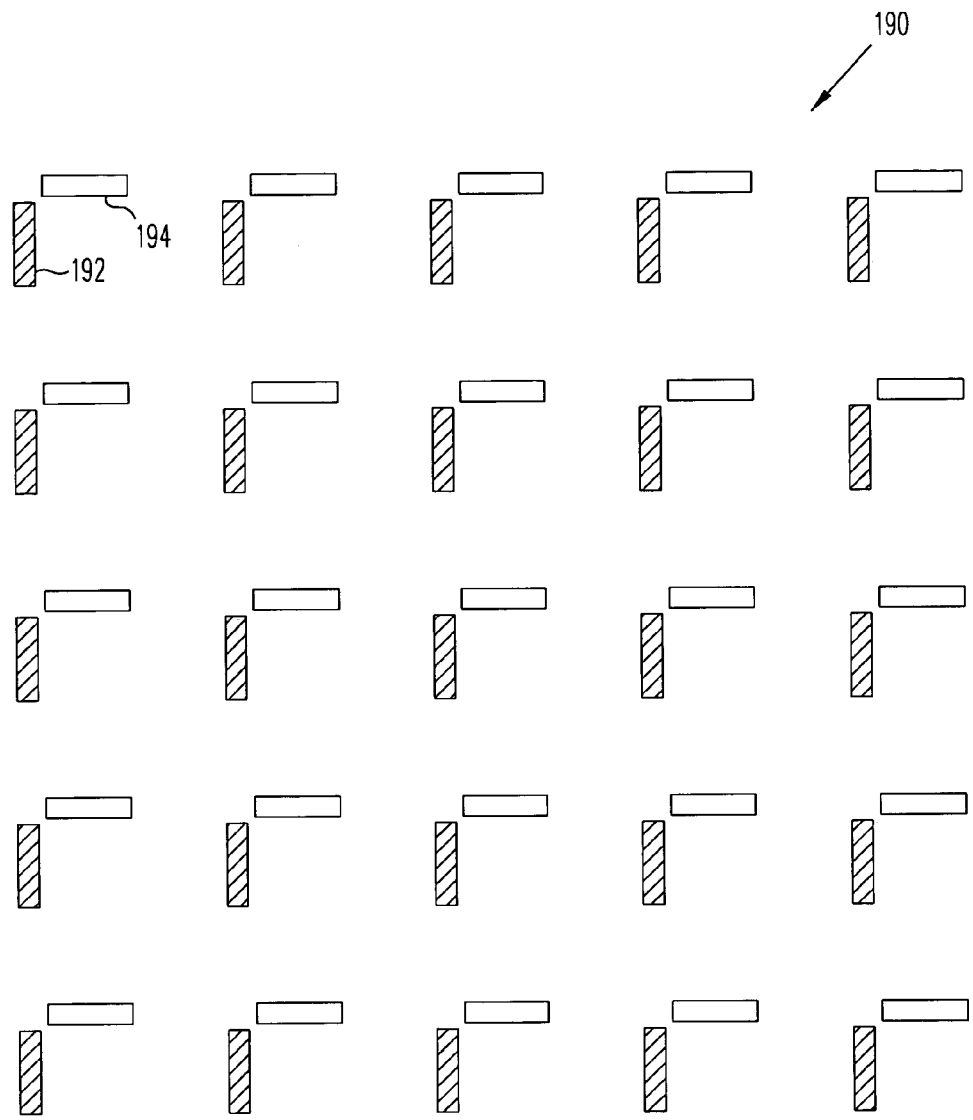
FIG. 11 is a top view of another embodiment of a two-dimensional overlay target.

FIG. 11 is a top view of another two-dimensional overlay target 190, which is similar to overlay target 180 and where the shaded targets 192 are on the bottom layer and the clear targets 194 are on the top layer.

An appropriate spectrophotometer, such as spectrometer 120 shown in FIG. 3A, may be used to measure two-dimensional overlay target 180 or 190. Any application of electromagnetic theory that allows the physical parameters of the overlay grating structure to be modeled such as RCWA, the Rayleigh method, or the Waterman method (P. C. Waterman, "Scattering by periodic surfaces." J. Acoustic. Soc. Am., 57, 791–802, (1975) and M. Bagieu and D. Maystre, "Waterman and Rayleigh methods for diffraction grating problems: extension of the convergence domain." J. Opt. Soc. Am. A, 15 (6), 1566–1576, (1998), both of which are incorporated herein by reference) may be used with spectrometer 120 to measure the relative shift in both the x and y directions of the overlay target 180.

Figure 12:
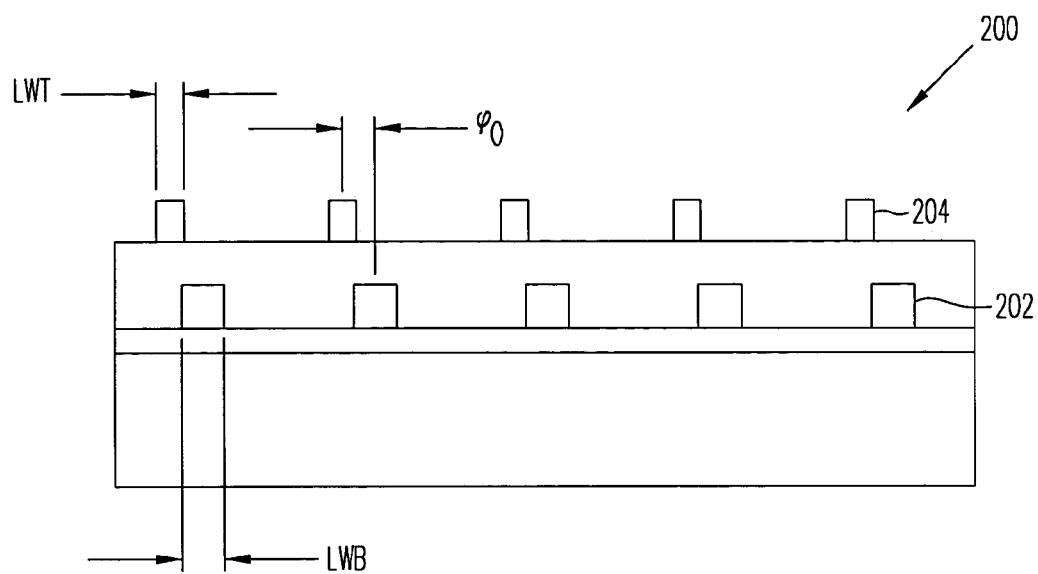
FIG. 12 shows a cross-sectional view of an overlay target having an asymmetry in offset phase and pitch.

It should be understood that the asymmetry of the overlay target is not limited to the phase, but may include other parameters. FIG. 12, for example, shows a cross-sectional view of an overlay target 200 where the line width LWB of the bottom diffraction grating 202 is different than the line width LWT of the top diffraction grating 204. The overlay target 200 also has an offset phase $\phi_0$ measured from the center lines in the bottom diffraction grating 202 and the top diffraction grating 204.

Figure 13:
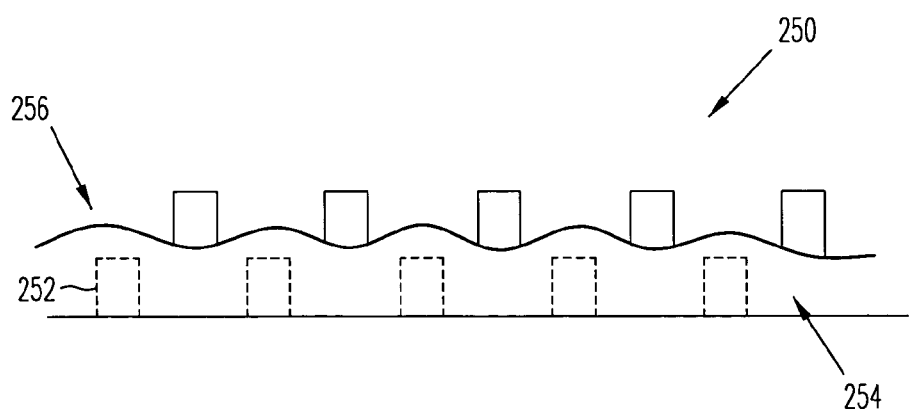
FIG. 13 shows a cross-sectional view of an overlay target having an opaque layer over the bottom diffraction grating.

Because spectrometer 120 in FIG. 3A uses the zero order diffracted light from both top diffraction grating 104 and bottom diffraction grating 102, the overlying layer 110 should be at least partially transparent to the wavelengths of light used by spectrometer 120. If an overlaying layer, i.e., a layer separating the top diffraction grating and bottom diffraction grating, is opaque, however, the overlay error may still be determined based on surface undulations in the overlaying layer. FIG. 13 shows an overlay target 250 where the bottom diffraction grating 252 is unobservable because of an opaque overlaying layer 254. Surface undulations 256, however, appear due to imperfect planarization of the opaque layer 254 after deposition. These undulations 256 have a period characteristic of underlying topography, i.e., bottom diffraction grating 252 and may be treated as a shallow grating for the overlay measurement. Thus, using the undulations 256 and the top diffraction grating 258 the overlay measurement may be made.

Figure 14:
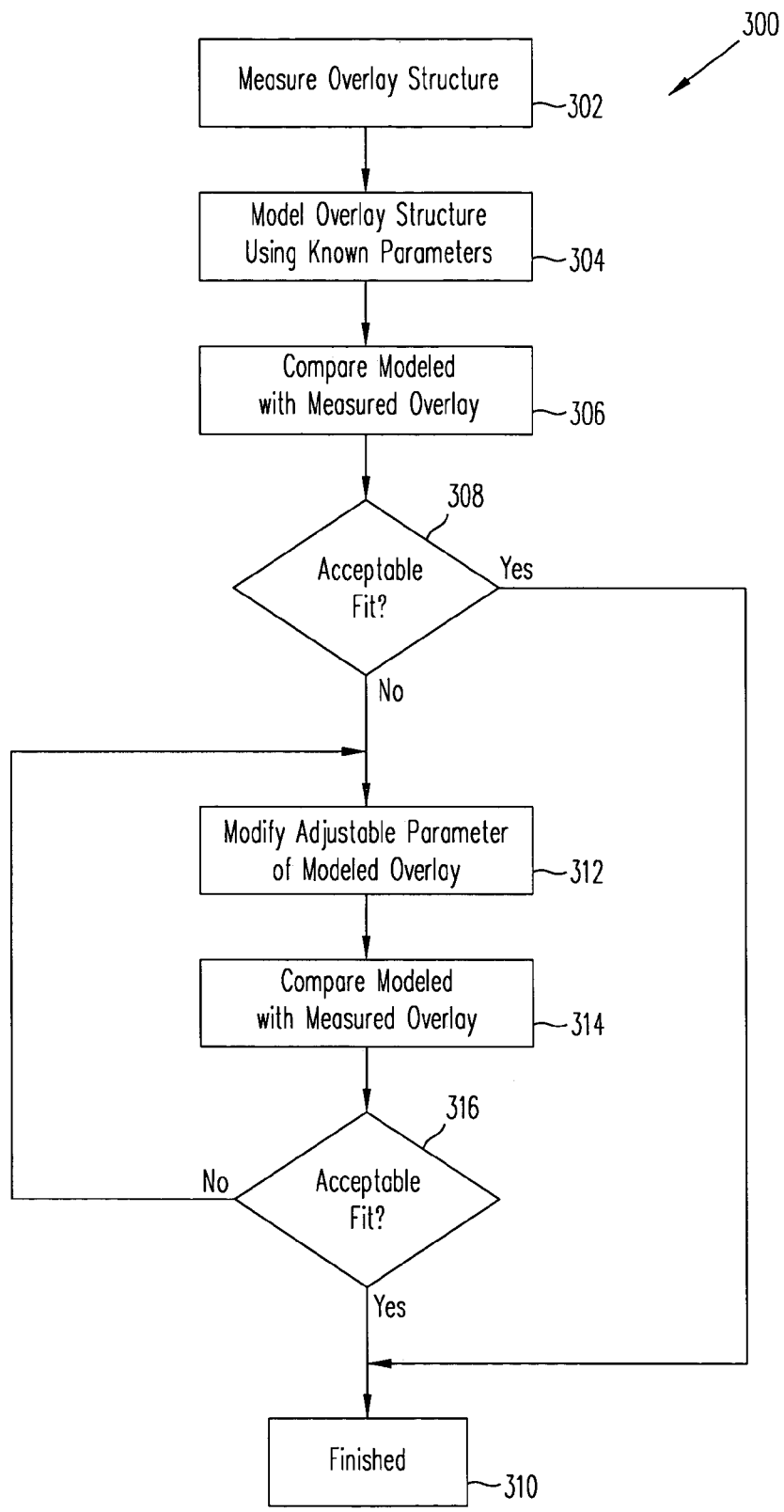
FIG. 14 is a flow chart of a process that may be used to spectroscopically measure an overlay target in accordance with the present invention.

FIG. 14 is a flow chart 300 of a process that may be used to spectroscopically measure an overlay target. Process 300 is similar to that described in Ser. Nos. 09/670,000 and 09/844,559, which are incorporated herein by reference. The overlay target is measured using a spectroscopic instrument, such as spectrometer 120 shown in FIG. 3A (block 302). The overlay target including the reflectance is modeled (block 304), for example, where the top diffraction grating is in the desired reference position. The RCWA process may be used, advantageously, to model complex targets, e.g., where spacers are present in the grating structure, e.g., a material different from the grating structure is deposited to cover the side of the bottom grating, this may be modeled using the RCWA process. The modeled reflectance is compared to the measured reflectance (block 306) and if there is an acceptable fit (block 308), according to a predetermined threshold, the process is finished (block 310) with the modeled overlay target accurately describing the physical overlay target, i.e., the top diffraction grating is aligned with the bottom diffraction grating.

If the fit is not acceptable (block 308), the adjustable parameter, such as the phase shift $\phi$, is adjusted using e.g., the Levenberg-Marquardt non-linear multivariate regression process. The regression analysis may include adjustments to phase-shift, linewidth (top and bottom), layer thicknesses, sidewall angles of the grating lines, and pitch (both top and bottom). If desired, detailed line-profiles rather than simple side wall angles may be used, however, the computation cost will be increased. The overlay target and its reflectance are again modeled (block 312) and compared to the measured overlay target (block 314). If the fit is acceptable (block 316), the process is finished (block 310), with the phase shift error known, i.e., the phase shift error is the offset phase shift $\phi_0$ subtracted from the measured phase shift. If the fit is not acceptable (block 316) the adjustable parameter is again adjusted (block 312) and the process continues until an acceptable fit is found.

Additionally, if desired, libraries may be used to increase the speed of calculation. Thus, for example, after diffracted light is detected from the overlay target, the detected light is compared to a library of diffracted light to determine the overlay error. If desired, further refinement of the overlay error may be determined using, e.g., the RCWA method described above. Alternatively, modal analysis may be used in a manner similar to the RCWA method.

As discussed above, the materials and physical dimensions of the overlay target, in accordance with the present invention, may vary. For example, the materials, line heights, and the separation distance between the top and bottom diffraction gratings, in the overlay target are often process dependent and are, thus, fixed parameters. The overlay target, however, includes several variable parameters, including the top and bottom line width (LWT and LWB), the pitch (P) and the offset phase shift $\phi_0$. Thus, in accordance with an embodiment of the present invention, the variable parameters of the overlay target are optimized for sensitivity based on the known fixed parameters.

The overlay target may be optimized by generating a model of the overlay target using fixed parameters and at least one variable parameter and calculating the diffracted light signature for the model of the overlay target for a plurality of values of the variable parameter. Based on the diffracted light signature the optimized value of the variable parameter may be determined. In addition, the sensitivity of the model may be calculated based on the diffracted light signature and the optimized value of the variable parameter is determined using the calculated sensitivity. The optimization may be done for a single wavelength or a plurality of wavelengths of light.

Figure 15:
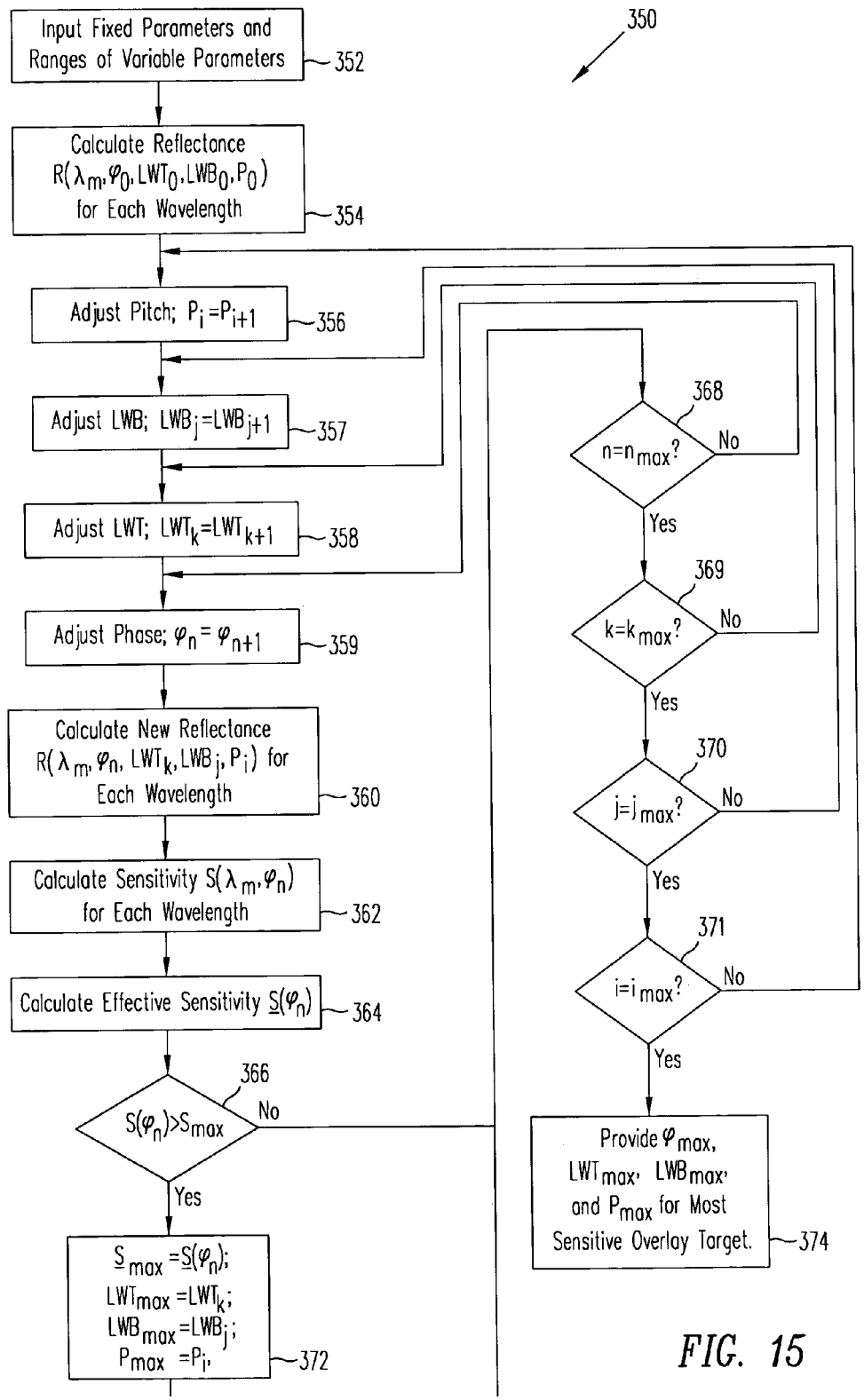
FIG. 15 is a flow chart of a process of optimizing an overlay target for spectroscopic sensitivity.

FIG. 15 is a flow chart 350 of an exemplary process of optimizing an overlay target for sensitivity. As shown in FIG. 15, the designer inputs the fixed parameters (block 352). The variable parameters ranges may also be input by the designer or may be based on the critical dimension (CD) as illustrated in Table 1.

TABLE 1

| Pitch | 2 CD to 15 CD |
|---|---|
| Top Line Width | 1/10 to 3/4 of Pitch |
| Bottom Line Width (1/3 to 3/4 of Pitch) | 1/10 to 3/4 of Pitch |
| Phase | 0 to 50% of Pitch |

The initial values of the variable parameters are set at the lowest (or highest) values of the ranges shown in Table 1. Alternatively, the initial values of the variable parameters may be set at the midpoint of each of the ranges.

The reflectance $R(\lambda_m, \phi_0, LWT_0, LWB_0, P_0)$ for the modeled overlay target is calculated for each wavelength (block 354), using for example the RCW process described above. The pitch P, bottom and top line widths, and phase $\phi$ are then adjusted as shown in blocks 356, 357, 358, and 359, respectively. The adjustments may be any desired amount, e.g., 1% to 10% of the range. Of course, smaller adjustments will result in a more accurate optimization, but will be more time consuming. Because this process is to optimize the variable parameters, as opposed to model a physical structure, an adjustment of approximately 5% of the ranges should be adequate.

The new reflectance is then calculated for each wavelength (block 360). The sensitivity for each wavelength relative to the phase can then be calculated as shown in equation 1 (block 362), and the effective sensitivity $S(\phi_n)$ is calculated as shown, e.g., in equation 3 (block 364).

The process then determines if the effective sensitivity $S(\phi_n)$ is greater than the maximum sensitivity $S_{max}$ (block 366). If the sensitivity is not greater, the process determines if $\phi$, LWT, LWB or P have been adjusted through the entire possible range (blocks 368, 369, 370, and 371). If $\phi$, LWT, LWB or P have not been adjusted through the entire range, the next adjustment is made in blocks 356–359.

If the effective sensitivity $S(\phi_n)$ is greater than a the maximum sensitivity $S_{max}$ (block 366), the current values of $S(\phi)$, LWT, LWB and P are set as the max values in block 372 and the process then determines if $\phi$, LWT, LWB or P have been adjusted through the entire possible range (blocks 368–371).

Once $\phi$, LWT, LWB or P have been adjusted through the entire possible range (blocks 368–371), the system provides the values $\phi_{max}$, $LWT_{max}$, $LWB_{max}$ and $P_{max}$ as the optimized values for the overlay target (block 374).

Of course, if desired, not all the variable parameters need be optimized. For example, the top and/or bottom line widths may be set at one value. In addition, the variable parameters may have a limited range of values. For example, the phase shift $\phi$ may be limited to range between 10% and 40% of the pitch. Also, the optimization may be performed for a single wavelength or a plurality of wavelengths.

Moreover, if desired, the variable parameters, such as pitch and top and bottom line widths may be optimized based on an already optimized parameter. In one embodiment, a primary variable parameter, e.g., phase, may be set to a predetermined value. For example, the predetermined value may be a value that is a predicted optimized value such as 25%. One or more secondary variable parameters, such as pitch or line widths, may then be optimized based on the primary variable parameter being set at the predetermined value. The secondary variable parameters are then set at their optimized values and the primary variable is then optimized. Accordingly, the variable parameters of the overlay target can be efficiently and relatively quickly optimized to provide a strong sensitivity to misalignment.

Although the invention has been described with reference to particular embodiments, the description is only an example of the invention's application and should not be taken as a limitation. Various other adaptations and combinations of features of the embodiments disclosed are within the scope of the invention as defined by the following claims.

What is claimed is:

1. An overlay target for measuring the alignment of layers on a substrate, said overlay target comprising:
    a first symmetrical grating on a first layer disposed over said substrate, said first symmetrical grating being a diffraction grating;
    a second symmetrical grating on a second layer disposed over said first symmetrical grating, said second symmetrical grating being a diffraction grating, wherein the second symmetrical grating is nominally positioned over the first symmetrical grating so that there is an asymmetry between said first symmetrical grating and said second symmetrical grating in the direction of the periodicity of the first symmetrical grating and the second symmetrical grating; and
    a third symmetrical grating disposed over said substrate, said third symmetrical grating being a diffraction grating comprised of a third plurality of parallel lines; and
    a fourth symmetrical grating disposed over said third symmetrical grating, said fourth symmetrical grating being a diffraction grating comprised of a fourth plurality of parallel lines substantially parallel to said third plurality of parallel lines, said third symmetrical grating and said fourth symmetrical grating are asymmetrical relative to each other, and said third plurality of parallel lines and said fourth plurality of parallel lines are substantially perpendicular to said first plurality of parallel lines and said second plurality of parallel lines.

2. The overlay target of claim 1, wherein said second symmetrical grating has an offset phase shift relative to said first symmetrical grating.

3. The overlay target of claim 2, wherein said first symmetrical grating has a pitch and said offset phase shift is between 5% to 40% of said pitch.

4. The overlay target of claim 3, wherein said offset phase shift is approximately 25% of said pitch.

5. The overlay target of claim 2, wherein said offset phase shift is along one axis of said first symmetrical grating.

6. The asymmetrical overlay target of claim 2, wherein said offset phase shift is along two axes of said first symmetrical grating.

7. The overlay target of claim 1, wherein said first symmetrical grating is comprised of a plurality of parallel lines having a first line width and said second symmetrical grating is comprised of a plurality of parallel lines having a second line width, said first line width being different than said second line width.

8. The overlay target of claim 1, further comprising at least one layer disposed between said first symmetrical grating and said second symmetrical grating.

9. The overlay target of claim 1, wherein said first symmetrical grating is comprised of a first plurality of parallel lines and said second symmetrical grating is comprised of a second plurality of parallel lines substantially parallel with said first plurality of lines.

10. A method of optimizing an overlay target for measurement, said overlay target comprising a first symmetrical diffraction grating and a second symmetrical diffraction grating disposed over said first symmetrical diffraction grating, said method comprising:
    (a) generating a model of said overlay target using fixed parameters and at least one initial variable parameter, wherein said at least one initial variable parameter is an offset phase between said first symmetrical diffraction grating and said second symmetrical diffraction grating;
    (b) calculating the reflectance of said model with the initial variable parameter;
    (c) adjusting the variable parameter;
    (d) calculating the reflectance of said model with the adjusted variable parameter;
    (e) calculating the sensitivity relative to said variable parameter;
    (f) repeating acts (c) through (e) for a plurality of values of said variable parameter, wherein said offset phase is adjusted for a plurality of values between at least zero and fifty percent of the pitch of at least one of said first symmetrical diffraction grating and said second symmetrical diffraction grating; and
    (g) determining at least one optimized value for said variable parameter using the calculated sensitivities.

11. The method of claim 10, further comprising:
    (h) adjusting a second variable parameter;
    (i) repeating acts (b) through (g);
    (j) repeating acts (h) through (i) for a plurality of values of said second variable parameter; and
    (k) determining the optimized value for said second variable parameter.

12. A method of optimizing an overlay target for measurement, said overlay target comprising a first symmetrical diffraction grating and a second symmetrical diffraction grating disposed over said first symmetrical diffraction grating, said method comprising:
    (a) generating a model of said overlay target using fixed parameters and at least one initial variable parameter;
    (b) calculating the reflectance of said model with the initial variable parameter;
    (c) adjusting the variable parameter;
    (d) calculating the reflectance of said model with the adjusted variable parameter;
    (e) calculating the sensitivity relative to said variable parameter;
    (f) repeating acts (c) through (e) for a plurality of values of said variable parameter; and
    (g) determining at least one optimized value for said variable parameter using the calculated sensitivities;
    wherein said model further includes a primary variable parameter, said initial variable parameter is a secondary variable parameter, said method further comprising:
    (h) setting the value of said primary variable parameter at a predetermined value;
    (i) optimizing said secondary variable parameter based on said primary variable parameter being set at said predetermined value;
    (j) setting said secondary variable parameter at an optimized value;
    (k) adjusting said primary variable parameter;
    (l) calculating the reflectance of said model with said optimized value for said secondary variable parameter and said adjusted primary variable parameter;

(m) calculating the sensitivity relative to said adjusted primary variable parameter;
(n) repeating acts (k) through (m) for a plurality of values of said primary variable parameter; and
(o) determining an optimized value for said primary variable parameter using the calculated sensitivities.

13. The apparatus of claim 1, wherein said first symmetrical grating and said second symmetrical grating have a first periodicity in a first direction and a second periodicity in a second direction.

* * * * *